US012186003B2

(12) United States Patent
Wallace

(10) Patent No.: US 12,186,003 B2
(45) Date of Patent: Jan. 7, 2025

(54) BI-DIRECTIONAL PNEUMATIC IMPACTOR FOR ORTHOPEDIC DEVICES

(71) Applicant: Moxie Medical, LLC, Indianapolis, IN (US)

(72) Inventor: Joshua W. Wallace, Indianapolis, IN (US)

(73) Assignee: Moxie Medical, LLC, Indianapolis, IN (US)

( * ) Notice: Subject to any disclaimer, the term of this patent is extended or adjusted under 35 U.S.C. 154(b) by 518 days.

(21) Appl. No.: 17/548,940

(22) Filed: Dec. 13, 2021

(65) Prior Publication Data

US 2022/0183735 A1 Jun. 16, 2022

Related U.S. Application Data

(60) Provisional application No. 63/125,567, filed on Dec. 15, 2020.

(51) Int. Cl.
*A61B 17/92* (2006.01)
*A61F 2/46* (2006.01)
*A61B 17/00* (2006.01)

(52) U.S. Cl.
CPC ............ *A61B 17/92* (2013.01); *A61F 2/4603* (2013.01); *A61B 2017/00544* (2013.01);
(Continued)

(58) Field of Classification Search
CPC ............. A61F 2002/4681; A61B 17/92; A61B 17/921; B25D 9/18
See application file for complete search history.

(56) References Cited

U.S. PATENT DOCUMENTS 348,870 A 9/1886 Trump
3,541,868 A * 11/1970 Hall .................. A61B 17/92
74/44

(Continued)

FOREIGN PATENT DOCUMENTS

GB 2115886 A 9/1983
WO 2006/122435 A1 11/2006
WO WO 2014/091454 A1 6/2014

OTHER PUBLICATIONS

Aesculap, Minimally Invasive Hip Surgery Instrument Kit MIOS, Webpage, Jun. 20, 2019, 7 pages, https://web.archive.org/web/20190620213304/https://www.medicalexpo.com/prod/aesculap/product-70641-663434.html.

(Continued)

*Primary Examiner* — David W Bates
(74) *Attorney, Agent, or Firm* — Maginot, Moore & Beck, LLP

(57) ABSTRACT

A bi-directional pneumatic impactor for imparting impact forces to an object. The impactor includes a support structure having at least one grip member and a piston reciprocally moveable along a piston axis. A pressure control system coupled with the support structure and adapted to be connected to a supply of pressurized air. The pressure control system reciprocatingly moves the piston along the piston axis to generate forceful impacts at one or both ends of the reciprocal movement. An impact transfer assembly disposed on the support structure is adapted to be coupled with the object whereby the impact transfer assembly transfers impact forces to the object in the driving and/or the retracting directions. A control spool may be used to control the supply of pressurized air to the piston cylinder. The impact transfer assembly may include a hammer pin extending axially through the piston.

25 Claims, 15 Drawing Sheets

(52) U.S. Cl.
CPC . *A61B 2017/924* (2013.01); *A61F 2002/4681* (2013.01); *A61F 2002/4694* (2013.01)

(56) References Cited

U.S. PATENT DOCUMENTS

| | | | |
|---|---|---|---|
| 3,838,741 A * | 10/1974 | Pepe | E02D 7/10 |
| | | | 173/136 |
| 3,990,351 A | 11/1976 | Sundin | |
| 5,057,112 A * | 10/1991 | Sherman | A61B 17/1659 |
| | | | 606/86 R |
| 5,108,400 A * | 4/1992 | Appel | B25D 9/02 |
| | | | 173/91 |
| 5,152,352 A | 10/1992 | Mandanis | |
| 5,163,519 A | 11/1992 | Mead et al. | |
| 5,485,887 A * | 1/1996 | Mandanis | B25D 17/06 |
| | | | 173/91 |
| 6,416,517 B2 | 7/2002 | Harder et al. | |
| 6,883,619 B1 | 4/2005 | Huang | |
| 6,932,166 B1 | 8/2005 | Kirsch | |
| 7,001,393 B2 | 2/2006 | Schwenke et al. | |
| 7,637,327 B2 | 12/2009 | Grunig | |
| 7,708,739 B2 | 5/2010 | Kilburn et al. | |
| 8,968,326 B2 | 3/2015 | Mani et al. | |
| 9,931,151 B2 | 4/2018 | Donald et al. | |
| 9,999,518 B2 | 6/2018 | Mani et al. | |
| 10,076,340 B2 | 9/2018 | Belagali et al. | |
| 10,342,591 B2 | 7/2019 | Pedicini | |
| 10,420,567 B2 | 9/2019 | Pedicini | |
| 10,595,879 B1 | 3/2020 | Litwak | |
| 10,603,050 B2 | 3/2020 | Pedicini | |
| 11,083,512 B2 | 8/2021 | Pedicini | |
| 11,134,962 B2 | 10/2021 | Pedicini | |
| 2012/0232562 A1 * | 9/2012 | Mani | A61F 2/4612 |
| | | | 606/100 |
| 2013/0118766 A1 | 5/2013 | Watanabe | |
| 2014/0262399 A1 * | 9/2014 | Cunningham | E04H 17/263 |
| | | | 173/133 |
| 2018/0338751 A1 | 11/2018 | Pedicini | |

OTHER PUBLICATIONS

Kincise, Learning From the Past to Create the Future, Brochure, 2019, 4 pages, DePuy Synthes.
International Search Report and Written Opinion of the International Searching Authority, PCT/US2021/063062, Apr. 7, 2022, 9 pages.
Xtract-All Spine (MKS1031) Universal Spinal Implant Removal System—Surgical Technique Guide, Shukla Medical, 2018, 12 pages.
Abele, Alexander, Thesis Report—The next generation of a Surgical Power Tool, Jan. 18, 2019, 128 pages, Umea Institute of Design.
Translation of Office Action for JP 2023-560245, mailed Jun. 5, 2024.

* cited by examiner

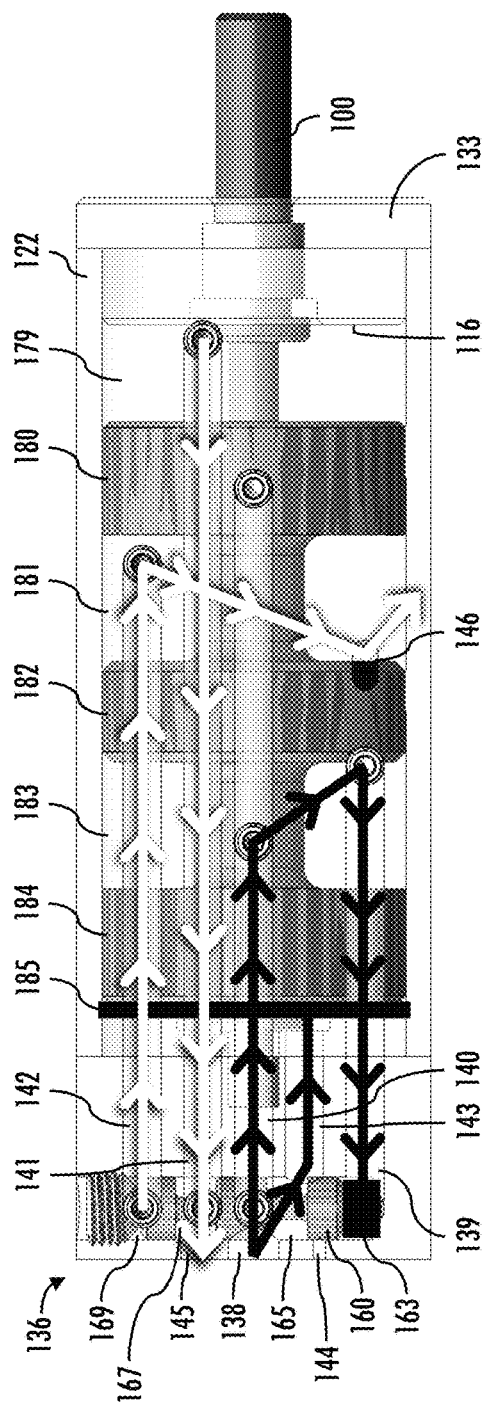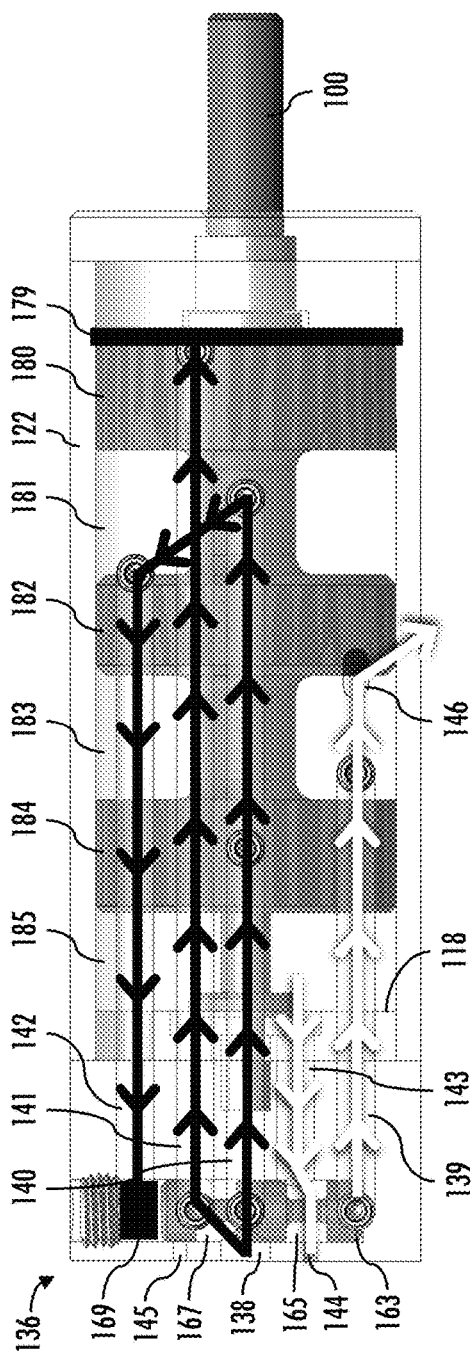

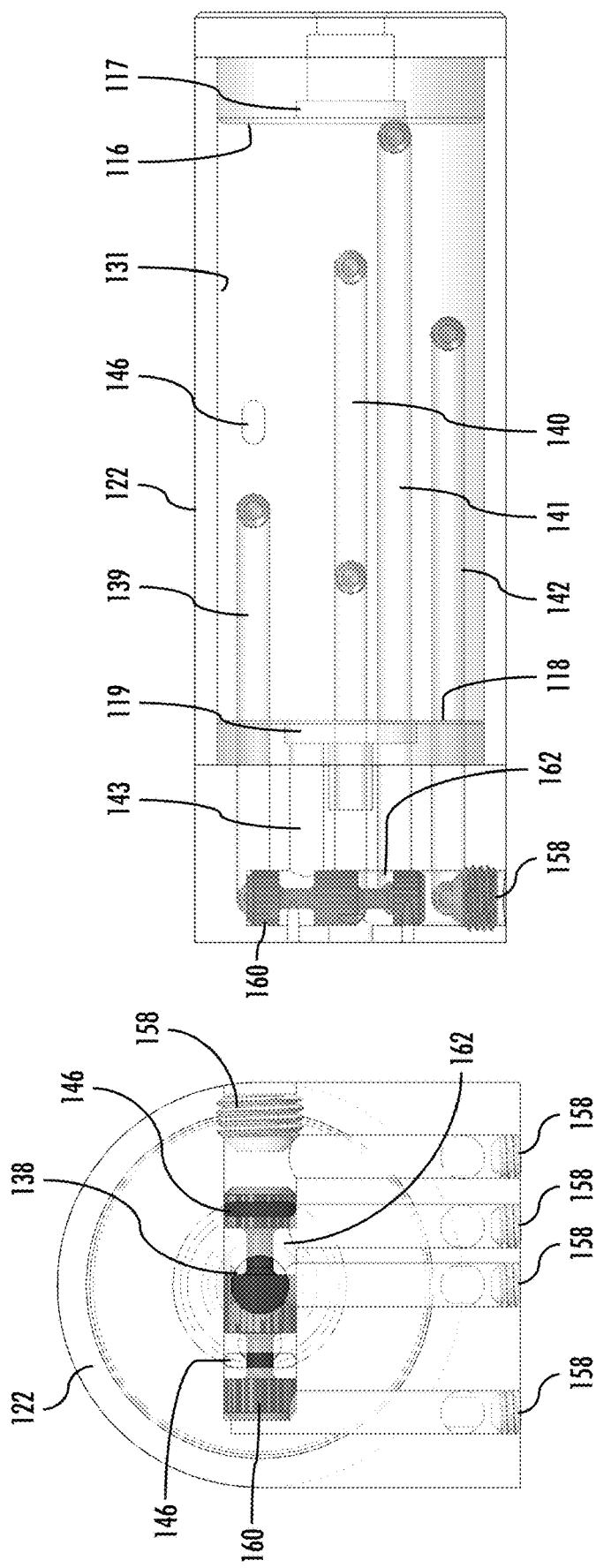

BI-DIRECTIONAL PNEUMATIC IMPACTOR FOR ORTHOPEDIC DEVICES

CROSS REFERENCE TO RELATED APPLICATIONS

This application claims priority under 35 U.S.C. 119(e) of U.S. provisional patent application Ser. No. 63/125,567 filed on Dec. 15, 2020 entitled BI-DIRECTIONAL PNEUMATIC IMPACTOR FOR ORTHOPEDIC DEVICES the disclosure of which is hereby incorporated herein by reference.

BACKGROUND

The present disclosure relates to surgical instruments useful in the implantation and/or removal of orthopedic implants and hardware.

When implanting or removing an orthopedic implant, it is often necessary to apply a series of impacts to the orthopedic implant either directly or through a secondary structure attached to the implant. In some situations, it is possible for the surgeon to generate such impacts using a mallet in the same manner a carpenter might impact a nail with a conventional hammer.

A variety of additional tools have also been developed for assisting the surgeon in applying such impacts. There remains a need, however, for an improved impactor that can be used in the implantation and/or removal of an orthopedic implant.

SUMMARY

The present disclosure provides a bi-directional pneumatic impactor that can be used in both the implantation and removal of orthopedic implants.

The invention comprises, in one form thereof, a bi-directional pneumatic impactor for imparting impact forces to an object that includes a support structure defining a piston cylinder and at least one grip member whereby a user can manually grasp the support structure; a piston reciprocally moveable along a piston axis within the piston cylinder; a pressure control system coupled with the piston cylinder and adapted to be connected to a supply of pressurized gas, wherein the pressure control system is adapted to reciprocatingly move the piston along the piston axis; an impact transfer assembly disposed on the support structure and adapted to be coupled with the object whereby the impact transfer assembly transfers impact forces generated by the piston to the object; and wherein the pneumatic impactor is selectively switchable between a driving mode and a retracting mode wherein, in the driving mode, the piston generates forceful impacts at a first end of the reciprocal movement and the impact transfer assembly transfers impact forces generated at the first end of the reciprocal movement to the object; and, in the retracting mode, the piston generates forceful impacts at a second end of the reciprocal movement opposite the first end and the impact transfer assembly transfers impact forces generated at the second end of the reciprocal movement to the object.

In some embodiments, the pneumatic impactor further includes a user-adjustable mechanism that adjusts the distance traveled by the piston or a user-adjustable pressure regulating valve that adjusts the pressure of the gas acting on the piston, either of which would adjust the speed of the piston at impact and thereby adjust the force of the impact.

In some embodiments, the pneumatic impactor is selectively switchable between the driving mode and the retracting mode by selectively configuring the pressure control system and the pneumatic impactor further includes a first spring which exerts a biasing force on the piston at the first end of the reciprocal movement and a second spring which exerts a biasing force on the piston at the second end of the reciprocal movement.

In such embodiments having a selectively configurable pressure control system, the impact transfer assembly may be disposed proximate the first end of the reciprocal movement and absorb impact forces from the piston when the pneumatic impactor is in the driving mode and the support structure may include a rigid housing member that extends from proximate the second end of the reciprocal movement to the impact transfer assembly and transfer impact forces to the impact transfer assembly when the pneumatic impactor is in the retracting mode.

In other embodiments, the pneumatic impactor is selectively switchable between the driving mode and the retracting mode by selectively configuring the impact transfer assembly wherein the impact transfer assembly includes an elongate hammer pin, the hammer pin being axially moveable relative to the piston and the support structure, the hammer pin including first and second impact surfaces wherein the first and second impact surfaces face in opposite axial directions and the piston is engageable with the first impact surface to impart impact forces to the hammer pin in a first axial direction and the piston is engagable with the second impact surface to impart impact forces to the hammer pin in an opposite second axial direction and wherein the hammer pin is axially movable relative to the housing between a first axial position wherein only the first impact surface of the first and second impact surfaces is engageable by the piston and a second axial position wherein only the second impact surface of the first and second impact surfaces is engageable by the piston.

In such embodiments having a hammer pin, the piston may define an axially extending central opening, wherein the elongate hammer pin extends through the central opening of the piston, the piston being reciprocatingly slidable on the hammer pin, and the first and second impact surfaces of the hammer pin being disposed on opposite first and second axial ends of the piston.

In the embodiments having a hammer pin, the hammer pin may have an axially extending end projecting from the support structure which is adapted to be coupled with the object.

In the embodiments having a hammer pin, the piston may be configured such that, at the first axial end of the piston, the piston defines a first axially outwardly facing contact surface engageable with the first impact surface when the hammer pin is in the first axial position and a first axially outwardly facing piston surface is engageable with the support structure when the hammer pin is in the second axial position, and, at the second axial end of the piston, the piston defines a second axially outwardly facing contact surface engageable with the second impact surface when the hammer pin is in the second axial position and a second axially outwardly facing piston surface engageable with the support structure when the hammer pin is in the first axial position.

In some embodiments of the pneumatic impactor, the pressure control system includes a control spool slidably disposed in a spool cylinder, the control spool controlling the supply of pressurized gas to the piston cylinder to thereby generate reciprocating movement of the piston.

In such embodiments having a control spool, the piston may include three axially spaced piston heads which divide the piston cylinder into four separate pressure chambers, the piston cylinder defining at least one piston vent passage and wherein at least one spool vent passage is in communication with the spool cylinder and wherein, in a first piston position wherein the piston is disposed in a proximal portion of the piston cylinder and the spool is disposed in a first spool position within the spool cylinder, the two most proximal piston chambers are supplied with pressurized gas and the two most distal piston chambers are vented to the atmosphere through the at least one piston vent passage and the at least one spool vent passage and pressurized air within the spool cylinder biasing the spool toward a second spool position, and, in a second piston position wherein the piston is disposed in a distal portion of the piston cylinder and the spool positioned in a second spool position, the two most distal piston chambers are supplied with pressurized gas and the two most proximal piston chambers are vented to the atmosphere through the at least one piston vent passage and the at least one spool vent passage and pressurized air within the spool cylinder biasing the spool toward the first spool position. In such embodiments, the at least one spool vent passage may take the form of two spool vent passages wherein the spool blocks the venting of air through one of the spool vent passages in the first spool position and blocks the venting of air through the other one of the spool vent passages in the second spool position.

In any of the embodiments described above, the pneumatic impactor may include a user-adjustable pressure valve for adjusting the pressure of the gas acting on the piston.

In any of the embodiments described above, the pneumatic impactor may include an impact transfer assembly that includes at least one strike surface and at least one pull surface wherein the at least one strike surface faces in a first axial direction and the at least one pull surface faces in a second axial direction opposite the first axial direction.

In embodiments having such strike and pull surfaces, the strike and pull surfaces may be defined by a quick-release chuck assembly. In an alternative embodiment, the strike surface may be defined by a strike member with the strike surface forming a planar surface intersecting the piston axis at a perpendicular angle, and wherein the impact transfer assembly includes a plurality of latches circumferentially and symmetrically disposed about the strike surface, the at least one pull surface being formed by a plurality of pull surfaces with each of the plurality of latches defining one of the plurality of pull surfaces and wherein each of the plurality of latches is moveable between an unengaged position and an engaged position wherein, when the plurality of latches are in the unengaged position, the plurality of latches allow the object to be engaged with the strike surface and, when the plurality of latches are in the engaged position with the object engaged with the strike surface, each of the plurality of latches engage the object with a corresponding one of the plurality of pull surfaces to thereby secure the object between the strike member and the plurality of latches.

In any of the embodiments described above, the at least one grip member may take the form of first and second grip members with the piston axis being symmetrically disposed between the first and second grip members. The piston may also be disposed in an elongate central housing member of the support structure, wherein the elongate central housing member extends parallel with the piston axis between first and second opposing ends of the central housing member and the first and second grip members are disposed on opposite sides of the central housing member and are axially positioned between the first and second opposing ends of the central member.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein:

FIG. 10A is similar to FIG. 10 but also includes arrows schematically depicting the flow of gas within the main body.

FIG. 11A is similar to FIG. 11 but also includes arrows schematically depicting the flow of gas within the main body.

FIG. 14 is a transparent end view of the main body of the second embodiment showing alternative spool vent passages.

FIG. 15 is a transparent side view of the main body of FIG. 14 with the piston and hammer pin removed.

Figure 1:
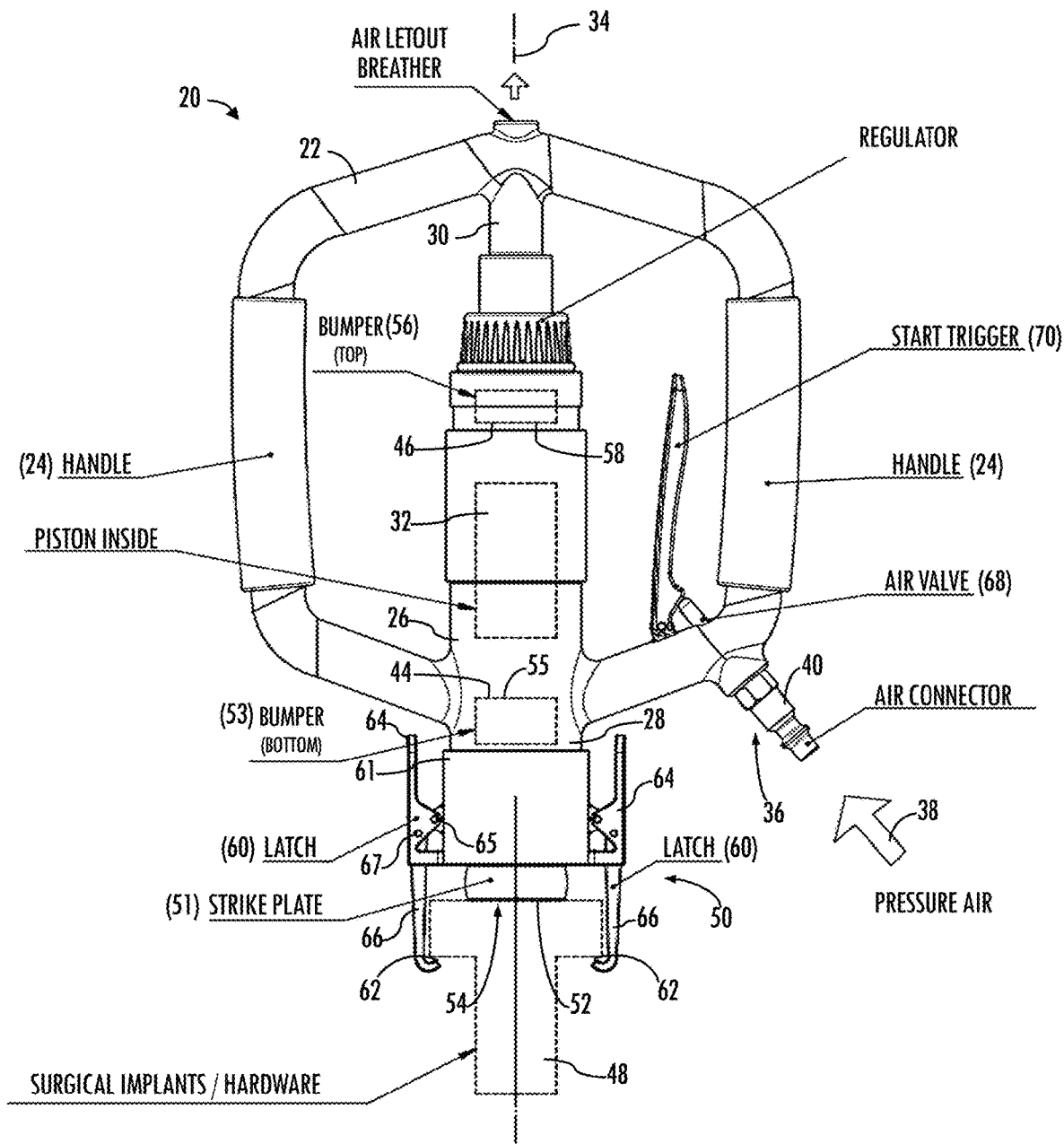
FIG. 1 is a front view of a first embodiment of a bi-directional pneumatic impactor.

Corresponding reference characters indicate corresponding parts throughout the several views. Although the exemplification set out herein illustrates embodiments of the invention, in multiple forms, the embodiments disclosed below are not intended to be exhaustive or to be construed as limiting the scope of the invention to the precise forms disclosed.

DETAILED DESCRIPTION

The following description includes a description of two different embodiments and a variety of modifications that may be made to either one or both of the two main embodiments, however, further modifications utilizing the teachings set forth herein may also be used within the scope of the present disclosure.

First Embodiment (FIGS. 1-5)

A first embodiment 20 of a bi-directional pneumatic impactor is shown in FIGS. 1-5. Impactor 20 includes a support structure 22 defining a piston cylinder 31 and having a pair of grip members 24 located on opposite sides of an elongate central housing member 26. The two grip members 24 are each attached to the central housing member 26 at two locations, one of the locations being proximate the first end 28 of the central housing member 26 and the other location being proximate the second end 30 of the central housing member 26. Central housing member 26 is symmetrically disposed between grip members 24 whereby a user manually grasping the grip members 24 can securely hold the impactor 20 and easily control the position and movement of impactor 20 during use.

A piston 32 is moveably disposed within piston cylinder 31 and reciprocates along a piston axis 34. In the illustrated embodiment, piston 32 is disposed in elongate central housing member 26 which defines piston cylinder 31. Housing member 26 extends parallel with piston axis 34 between the opposing ends 28, 30 of housing member 26. The two grip members 24 are disposed on opposite sides of the central housing member 26 and are axially positioned between the opposing ends 28, 30 of central member 26 which thereby positions the reciprocating piston between the two hands of the user which facilitates the user's control and positioning of impactor 20 during use. Advantageously, the impactor 20 has a total weight of no more than 3 to 5 pounds (1.36 to 2.27 kg). In the illustrated embodiment, support structure 22 is formed out of stainless steel tubing and impactor 20 has a total weight of approximately 2 to 3 pounds (0.91 to 1.36 kg) with piston 32 having a weight of approximately 1 pound (0.45 kg). It is further noted that the dimensions set forth in the figures are in inches.

Impactor 20 includes a pressure control system 36 which is mounted on or coupled with the support structure 22 and is connectable to a supply of pressurized gas 38. In the illustrated embodiment, impactor 20 includes a connector 40 which is in communication with the pressure control system 36 and mounted on support structure 22 for connecting with gas supply 38.

A typical hospital operating room ("OR") will have a pressurized gas supply that is a permanent fixture of the OR and which can be connected to a pneumatic device using conventional hoses and connectors. Such gas supplies are often wall mounted and have internal gauges that monitor and regulate the pressure of the gas that is being supplied to a connected device. Such systems are often referred to as pressurized air systems and while such systems often use pressurized air, such systems and the pneumatic devices disclosed herein, are not limited to pressurized air and might also employ other pressurized gases. In accordance with such conventional usage, the term "pressurized air" and variants thereof, should not be interpreted as being limited solely to a pressurized gas having the exact composition as the surrounding ambient air but shall encompass all pressurized gases unless it is specifically noted that such term excludes alternative gases and gas compositions. Impactor 20 is well-suited for use with the typical pressurized gas supply 38 found in most ORs.

The user of impactor 20 can switch pressure control system 36 between a driving mode and a retracting mode to thereby provide impactor 20 with bi-directional functionality. In the driving mode, pressure control system 36 moves piston 32 in a reciprocating motion along piston axis 34 with piston 32 generating forceful impacts at a first end 44 of the reciprocal movement of the piston. In the retracting mode, pressure control system 36 moves piston 32 in a reciprocating motion along piston axis 34 with piston 32 generating forceful impacts at a second end 46 of the reciprocal movement opposite the first end 44.

A user-adjustable pressure regulating valve may be used to adjust the air pressure acting on the piston to thereby adjust the magnitude of the impacts generated by the piston. The operation of pressure control system 36 is discussed in greater detail below.

Impactor 20 also includes an impact transfer assembly 50. Assembly 50 is attached at the end 26 of central housing member 26 and transfers the impacts generated by piston 32 to the object 48 being either driven or retracted. Impactor 20 is well-suited for driving and retracting orthopedic implants such intramedullary nails, total joint implants and other orthopedic hardware. Such orthopedic implants often include specifically designed holders that grasp the implant and are designed to receive the impacts of a mallet or other device. When employing impactor 20 with an implant having such a holder, the impact transfer assembly 50 would be engaged with the holder rather than the implant itself and thereby transfer the impacts to the implant via the holder. Object 48 in FIG. 1 represents such a holding device for an orthopedic implant. It is also noted that many orthopedic implant manufacturers employ connections that are unique to their own products. A variety of impact transfer assemblies 50 can be employed and interchanged on impactor 20 whereby impactor 20 can be used with implants from a variety of different manufacturers having different connection configurations. For example, impact transfer assembly 50 may have a collar with an internal helical thread that engaged an external helical thread on central housing member 26 whereby one transfer assembly 50 adapted for use with the connector of one manufacturer can be unscrewed from central housing member 26 and replaced by screwing on an alternatively configured impact transfer assembly 50 adapted for use with the connector of a different manufacturer.

When attached to support structure 22, impact transfer assembly 50 is disposed proximate the first end 44 of the reciprocal movement of piston 32 and absorbs impact forces from the piston when the pressure control system is in the driving mode and then transfers such forces to object 48 via a strike surface 52 that intersects the piston axis 34 and faces away from the support structure 22. In the illustrated embodiment, strike surface 52 is a planar surface defined by strike assembly 54. Strike assembly 54 also includes an impact surface 55 located opposite strike surface 52 that is impacted by piston 32 and defines the first end 44 of the reciprocal movement of piston 32. Strike surface 52 and impact surface 55 can both be located on a single unitary piece of material or be formed on separate parts that coupled together to communicate the transmission of impact forces from piston 32.

The illustrated strike assembly 54 includes a first strike member in the form of a strike plate 51 that defines strike surface 52 and a second strike member in the form of a cylindrical impact member 53 that defines impact surface 55. In the illustrated embodiment, strike plate 51 is fixed to the end of central housing member 26 where strike surface 52 can be used to impart impact forces to object 48. Impact member 53 has an external helical thread that engages an internal helical thread of central housing member 26 to secure impact member 53 in a position where impact surface 55 can be struck by piston 32. The use of helical threads to secure impact member 53 facilitates the adjustment of the axial position of impact member 53. Central housing member 26 is used to transfer impact forces from impact member 53 to strike plate 51.

Central housing member 26 of support structure 22 forms a rigid housing member that extends from proximate the second end 46 of the reciprocal movement of piston 32 to the impact transfer assembly 50 and also transfers impact forces to the impact transfer assembly 50 when the pressure control system 36 is in the retracting mode. In the illustrated embodiment, impact member 56 defines an impact surface 58 that functions as the second end of the reciprocal movement of piston 32 and which is impacted by piston 32. The impact forces generated by piston 32 striking impact surface 58 are transferred to central housing member 26 by securing impact member 56 relative to housing member 26. Housing member 26 then transfers these impact forces to impact transfer assembly 50.

Impact transfer assembly 50 includes pull surfaces 62 that are disposed axially outwardly of the strike surface 52 and which face toward the support structure 22 whereby impact surfaces generated during the retraction mode can be transferred to object 48. In the illustrated embodiment, pull surfaces 62 are located on a plurality of latches 60 which are circumferentially and symmetrically disposed about the strike surface 52. In the illustrated embodiment, there are two latches 60 which are located diametrically opposite each other.

Figure 3:
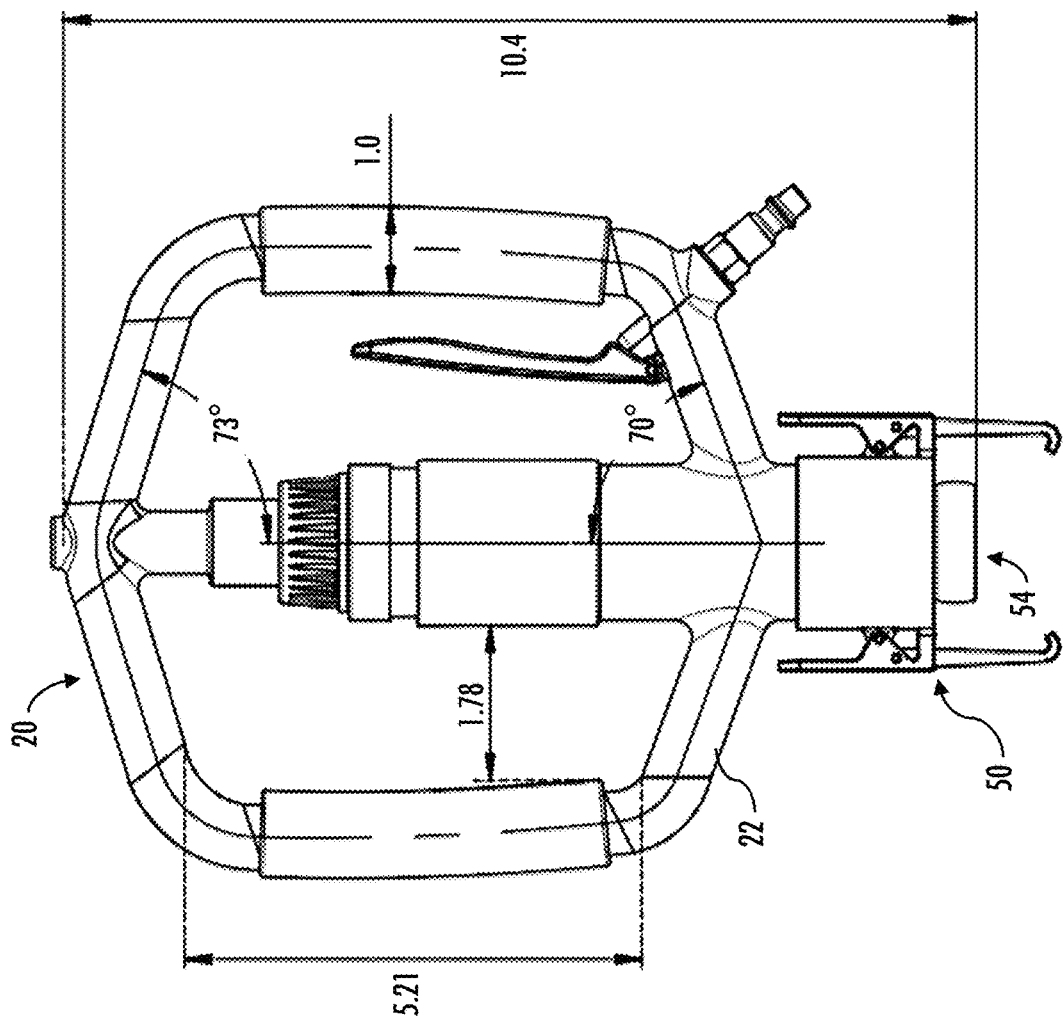
FIG. 3 is another front view of the first embodiment.
Figure 2:
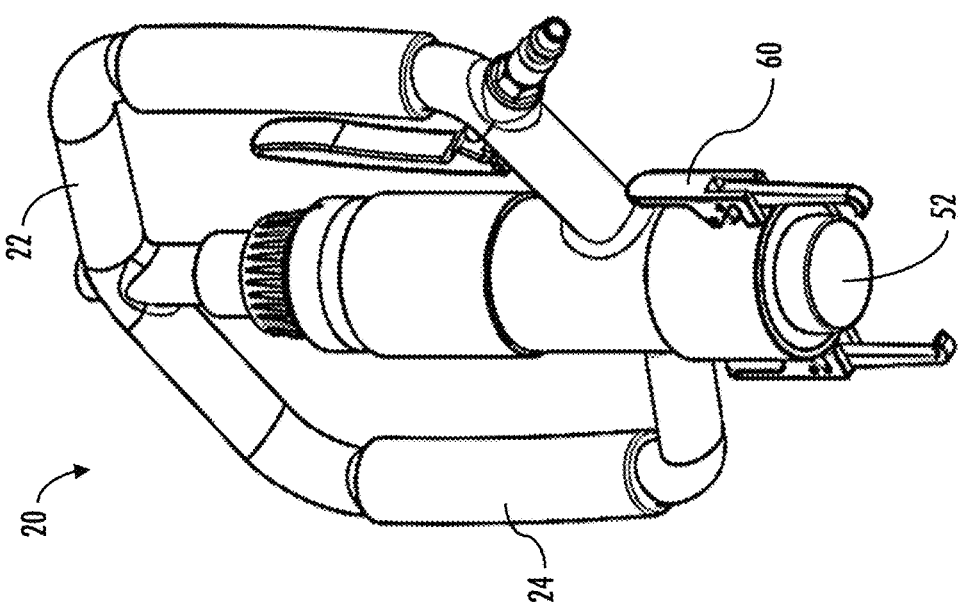
FIG. 2 is a perspective view of the first embodiment.
Figure 4:
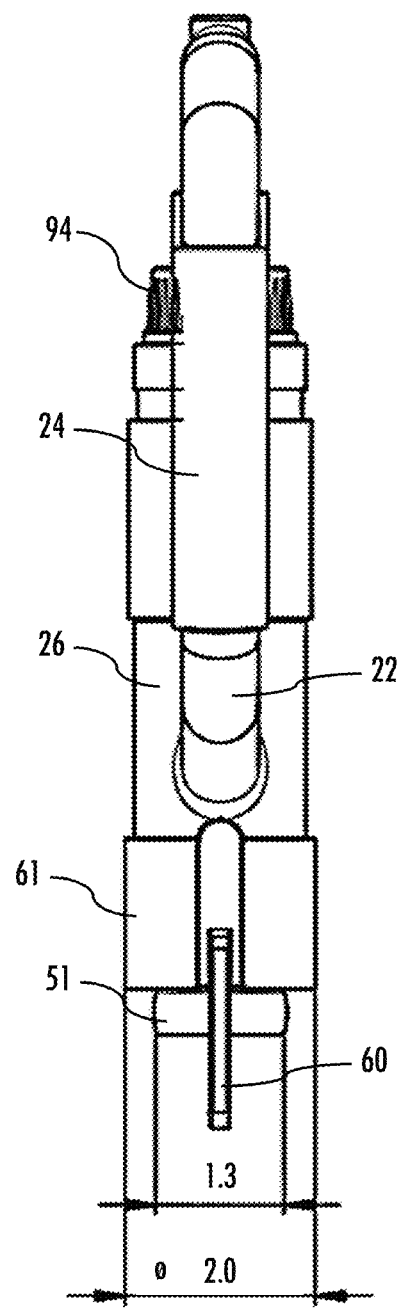
FIG. 4 is a side view of the first embodiment.

Each of the latches 60 is moveable between an unengaged position (shown in dashed outline in FIG. 3 and an engaged position (solid lines in FIGS. 1-4) wherein, when the latches are in the unengaged position, the latches allow object 48 to be engaged with strike surface 52, and, when the plurality of latches are in the engaged position with object 48 engaged with strike surface 52, the latches engage the object with a corresponding one of the pull surfaces 62 to thereby secure object 48 between the strike member/strike plate 51 and the plurality of latches 60. Moving the latches 60 to the disengaged position also allows object 48 to be disengaged from impactor 20. In the illustrated embodiment, latches 60 are dual pivoting latches having a lever member 64 pivotally mounted to impact transfer assembly 50 with pivot pin 65 and a grip member 66 pivotally mounted to lever member 64 with pivot pin 67.

In the disclosed embodiment, latches 60 are mounted on a collar 61 that is engaged with central housing member 26 with cooperating helical threads. By adjusting how far collar 61 is threaded onto central housing member 26, the axial distance between strike surface 52 and pull surfaces 62 can be adjusted to match the axial dimension of the object being grasped.

Alternatively, a quick-release chuck assembly may be form a part of the impact transfer assembly and be used to connect impactor 20 with the object to be driven or retracted. One example of such a quick-release chuck assembly is discussed in greater detail in description of the second embodiment.

Other forms of impact transfer assemblies may also be employed. For example, instead of using a strike plate and latches to form the strike and pull surfaces, a helically threaded member could be used to threadingly engage the object to be impacted. With such a helically threaded member, that side of thread that faced away from the support structure would act as the strike surface and that side of the thread that faced toward the support structure would act as the pull surface. Various other forms of gripping an object in a manner that allows for the transfer of impact forces may also be used. For example, while the strike surfaces of the illustrated embodiments define a plane perpendicular to piston axis 34, it is not necessary for the strike or pull surfaces to be perpendicular to the piston axis. Instead, the strike surface may face in a direction that forms a perpendicular or non-perpendicular angle with the piston axis so long as it defines a direction that extends at least partially in a first axial direction while the pull surfaces face in a second direction that extends at least partially in a second axial direction opposite the first axial direction.

As mentioned above, impactor 20 includes a pressure control system 36 having a connector 40 that couples the pressure control system 36 with a source of pressurized gas 38.

Figure 5:
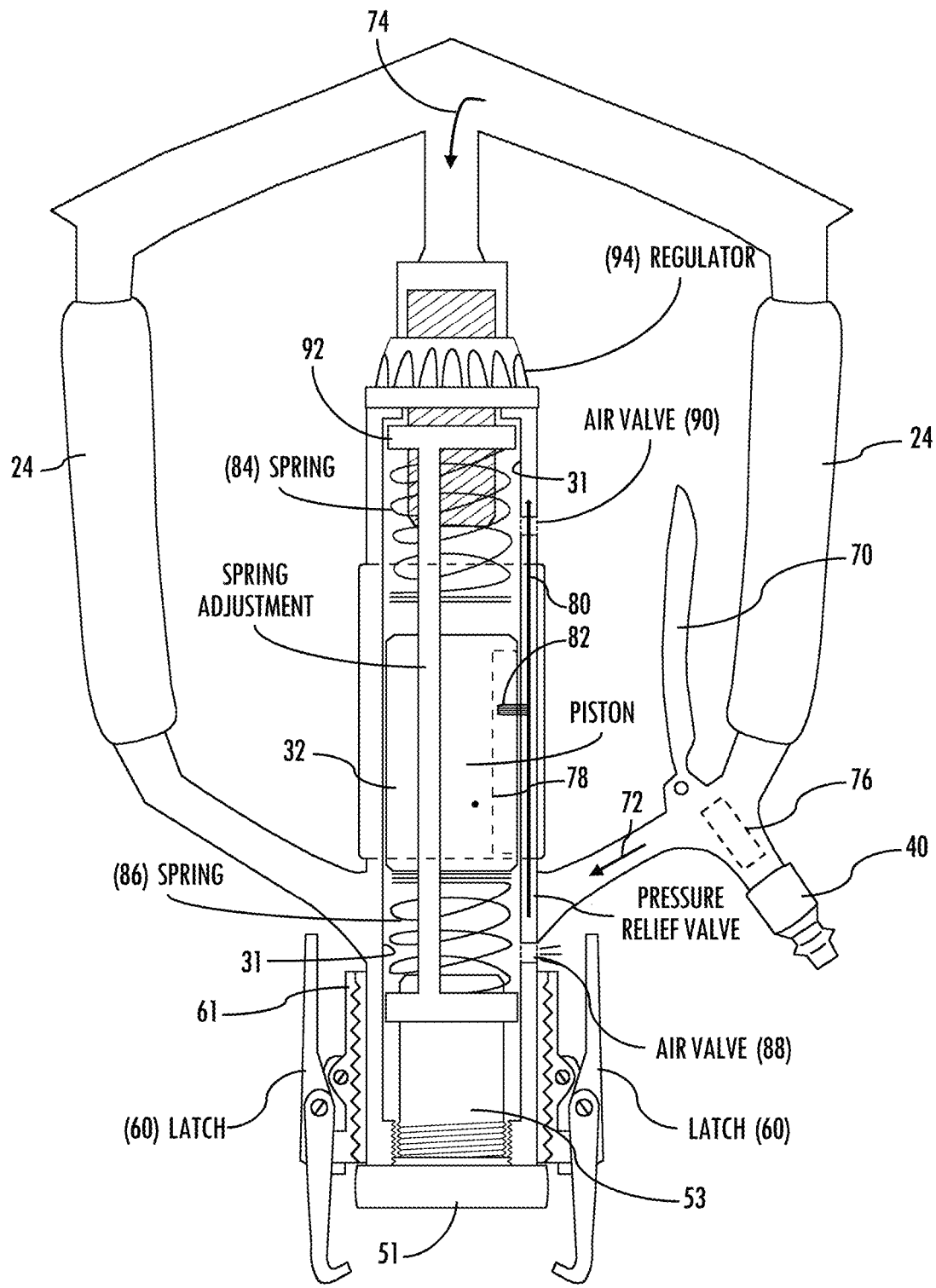
FIG. 5 is a schematic diagram of the first embodiment.

The operation of air pressure control system 36 is best understood with reference to FIG. 5 in addition to FIGS. 1-4. When connected to a source of pressurized gas 38, a valve 68 (FIG. 5) operated by activation lever 70 is used to control whether the pressurized air reaches piston 32. With lever 70 in the position shown in FIG. 1, valve 68 will be closed and prevent pressurized air from reaching piston 32. When the user moves lever 70 and holds it proximate the grip member 24 in the position indicated by a dashed outline in FIG. 3, valve 68 will be opened and impactor 20 will be activated.

When lever 70 is depressed, pressurized air is allowed to flow to the two opposing ends of the reciprocal movement of piston 32 as indicated by arrows 72, 74. The pressurized air may be conveyed either by having support structure 22 form an air-tight housing which conveys the pressurized air or by using air-tight tubes or hoses within support structure 22 to convey the pressurized air/gas.

Piston 32 includes an axially extending slot 78 that does not extend to the axial ends of piston 32. A valve control member 80 has a pin 82 that rides within slot 78. When impactor is in the driving mode, pressurized gas is conveyed as indicated by arrow 72 to force piston 32 towards impact member 56. As piston moves towards impact member 56 spring 84 is compressed. Valve control member 80 covers pressure relief opening 88 as the air pressure forces piston 32 towards impact member 56. (In FIG. 5, valve control member 80 is shown covering opening 90.) As piston 32 moves toward impact member 56, pin 82 eventually hits the end of slot 78 and further movement of piston 32 moves valve control member 80 axially until it uncovers pressure relief opening 88. Uncovering opening 88 allows spring 84 to propel piston 32 forcefully into strike member/impact member 53 to thereby generate an impact force that is transferred to object 48. This movement of the piston also causes valve control member 80 to move back to its original position due to engagement of the opposite end of slot 78 and recover opening 88 whereby the process of axially moving piston 32 towards impact member 56 with air pressure is begun again.

When impactor 20 is operated in the retracting mode, pressurized air is directed to the opposite side of piston 32 as indicated by arrow 74. The pressure would build on piston 32 to compress spring 86 until piston 32 had moved to an axial position that forced valve control member 80 to expose pressure relief opening 90 relieving the air pressure on piston 32 and allowing spring 86 to propel piston 32 towards impact member 56 where it would generate an impact force when it struck impact member 56. This movement of piston 32 would result in the movement of pressure control valve 80 and cause it to recover opening 90 whereby the process would repeat itself.

A user-operable selector valve 76 is used to determine whether impactor 20 is in the driving mode or the retraction mode. In the driving mode position, a selector valve 76, valve 76 directs pressurized air as indicated by arrow 72 and prevents pressurized air from being conveyed in the direction indicated by arrow 74. When switched to the retraction mode, valve directs pressurized air as indicated by arrow 74 and prevents it from being conveyed in the direction indicated by arrow 72. Selector valve 76 is positioned near where the pressurized air enters support structure 22 and may be separate from valve 68. Alternatively, a single valve unit might be used to provide the functionality of both valves 68 and 76. For example, lever 70 could be used to axially move a spool valve to turn on and off the supply of pressurized air while the rotational position of that spool valve could be used to determine which end of the piston that pressurized air was directed towards.

Springs 84, 86 are mounted in a spring holder 92. While spiral wound spring 84 encircles impact member 56, spiral wound spring 86 encircles the impact member 53 portion of strike assembly 54 that projects toward piston 32. Spring holder 92 and impact member 56 are axially repositionable by rotation of regulator cap 94. For example, regulator cap 94 may be threadingly engaged with central housing member 26 and have axially engaging surfaces that engage impact member 56 and spring holder 92 to axially position impact member 56 and spring holder 92 and absorb axially directed forces. By adjusting the travel distance of the reciprocal movement of piston 32 and the axial extent by which the spring responsible for generating the forceful impact is compressed, the magnitude of the forceful impacts generated by impactor 20 can be adjusted. Alternatively, one or both of spring holder 92 and impact member 56 may be independently axially repositionable. The axial length of spring holder 92 may also be independently adjustable to thereby control and adjust the resulting impacts generated by device 20.

When deployed, the user, e.g., a surgeon, would hold the two grip members 24 of impactor 20 and impactor 20 would then generate repeated impacts in the selected direction, either a driving impact imparted by strike surface 52 away from device 20 that would assist the surgeon in the insertion of an orthopedic implant or repeated impacts imparted by pull surfaces 62 that would assist the surgeon in removing an implanted orthopedic implant. In this regard, it is noted that the surgeon will generally find it useful to apply pressure in the direction in which it is desired to move the implant. This pressure will not only assist in moving the implant in the desired direction, it will also absorb the recoil generated by the spring when projecting the piston to create the forceful impacts applied to object 48.

Various other modifications may also be made to impactor 20. For example, an alternative pressure control system might be employed. For example, U.S. Pat. No. 348,870 issued Sep. 7, 1886 discloses a simple one directional valveless pneumatic hammer. The disclosed device might be modified to include a second set of openings and passageways with only one set be open at a time to thereby provide a reversible pneumatic impactor.

Second Embodiment (FIGS. 6-25)

Figure 25:
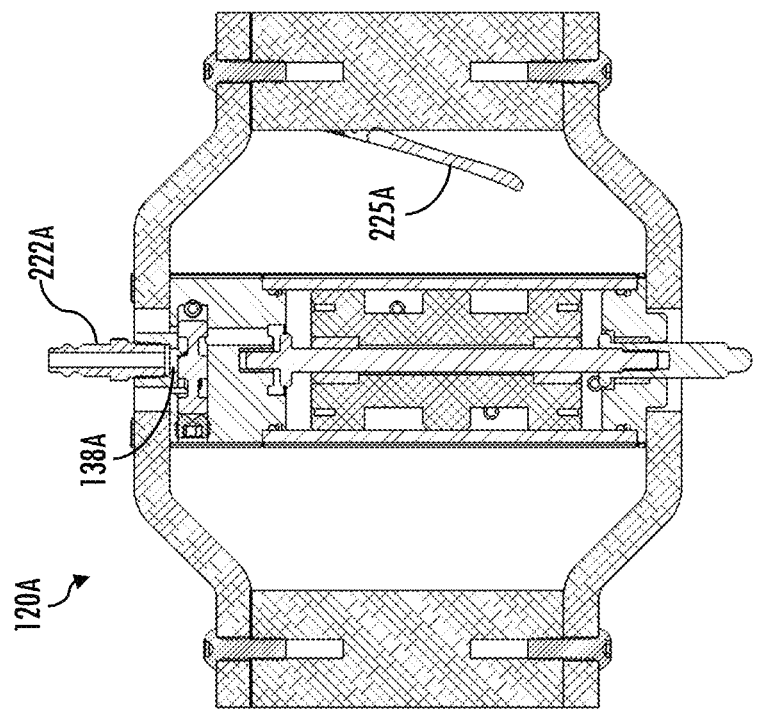
FIG. 25 is a cross sectional view of the modified impactor of FIG. 24.

FIGS. 6-23 and FIGS. 24 and 25 illustrate another embodiment of a bi-directional impactor. Similar to impactors 20 of FIGS. 1-5 which are selectively switchable between a driving mode and a retracting mode, impactors 120 of FIGS. 6-19 and impactors 120A of FIGS. 24 and 25 are also selectively switchable between driving mode and a retracting mode. As discussed above, the impactors 20 of FIGS. 1-5 achieve the selective switching between the driving and retracting mode by selectively altering the configuration of the pressure control system 36. As further discussed below, impactors 120, 120A achieve the selective switching between the driving and retracting mode by selectively altering the configuration of the impact transfer assembly 150.

Figure 7:
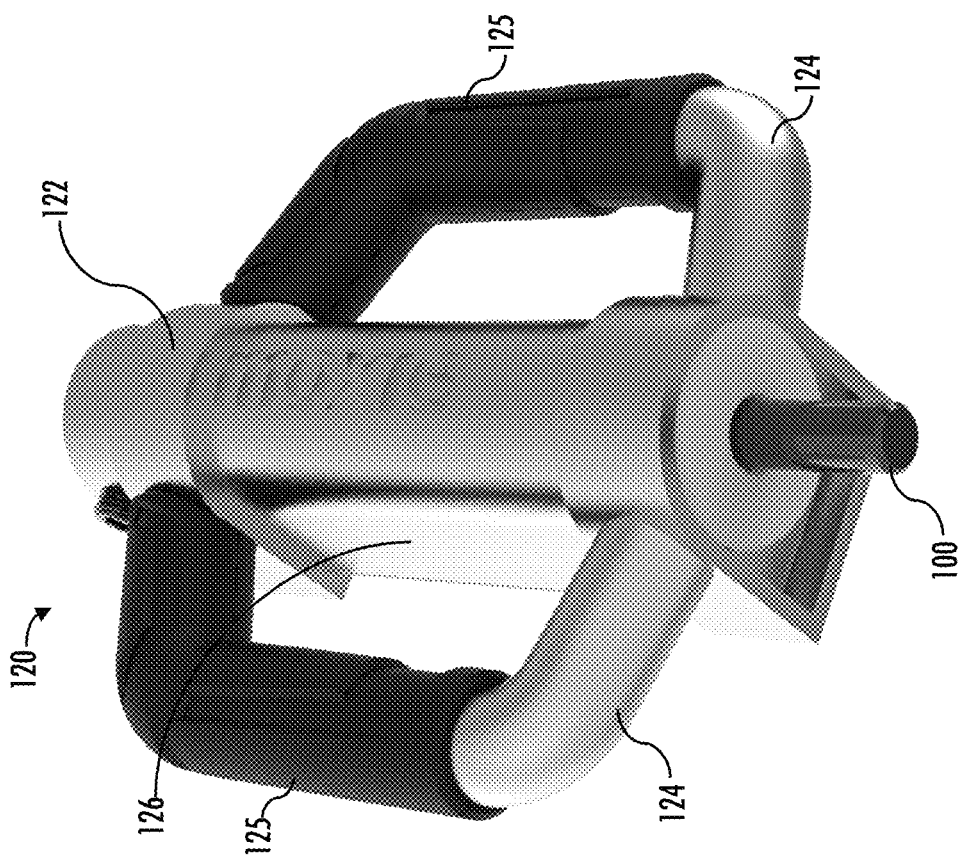
FIG. 7 is another perspective view of the second embodiment.
Figure 6:
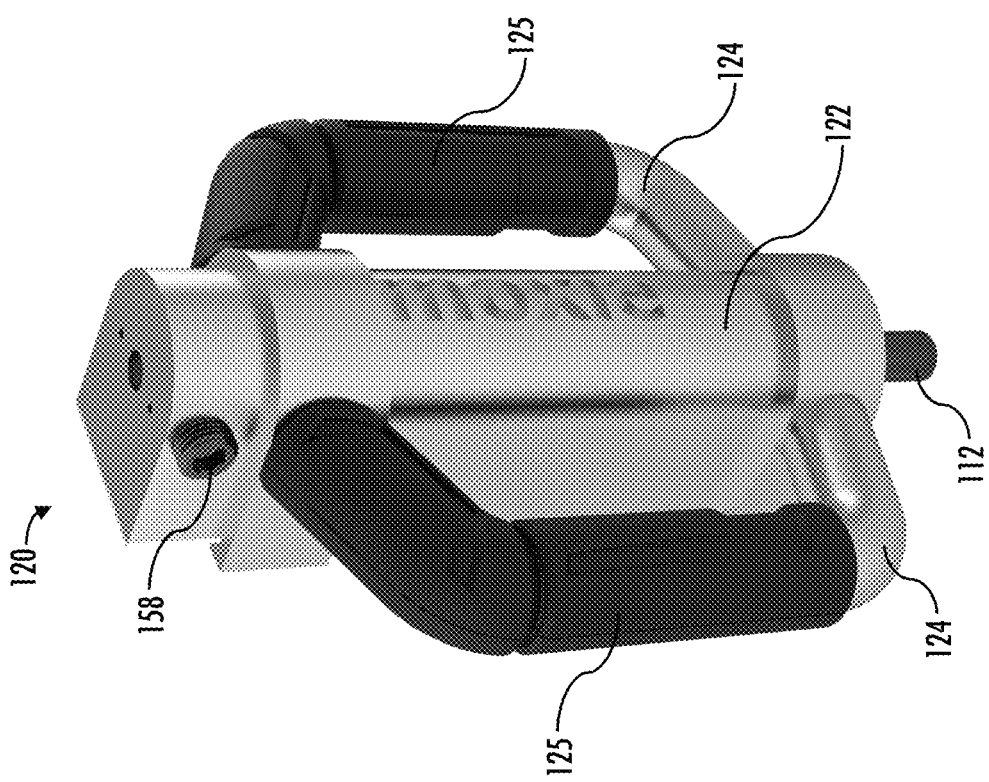
FIG. 6 is a perspective view of a second embodiment of a bi-directional pneumatic impactor.

Turning first to FIGS. 6 and 7, bi-directional pneumatic impactor 120 includes a support structure 122 defining a piston cylinder 131 and having a pair of grip members 124 located on opposite sides of an elongate central housing member 126. Housing member 126 extends parallel with piston axis 134 between the opposing ends 128, 130 of housing member 126. The two grip members 124 are axially positioned between the opposing ends 128, 130 of central member 126 which thereby positions the reciprocating piston between the two hands of the user which facilitates the user's control and positioning of impactor 120 during use.

To facilitate the understanding of how impactor 120 functions, FIGS. 8-16 show the central housing member 126 as transparent and do not show grip member 124. As can be understood with reference to these figures, a piston 132 is moveably disposed within piston cylinder 131 defined by elongate central housing member 126 and reciprocates along a piston axis 134 within piston cylinder 131.

A pressure control system 136 is coupled with the piston cylinder 131 and is adapted to be connected to a gas supply 38 whereby the pressure control system 136 moves piston 132 in a reciprocating motion along piston axis 134. In the embodiment of FIGS. 6-19, pressure control system 136 includes passages that are formed by bores central housing member 126, threaded caps 158 which seal some of the bores, a spool cylinder 162 and a control spool 160. The operation of pressure control system 136 is discussed in greater detail below.

Impact transfer assembly 150 includes a hammer pin 100. Hammer pin 100 is an elongate member having first and second impact surfaces 102, 104 that face in opposite axial directions. The hammer pin 100 is axially moveable relative to the support structure between two positions to selectively place pneumatic impactor 120 into either the driving mode or the retracting mode. In the driving mode, only impact surface 102 is engageable by piston 132 and in the retraction mode only impact surface 104 is engageable by piston 132. In the driving mode, when piston 132 is at the end of its reciprocal motion opposite impact surface 102 it strikes an interior wall of the piston cylinder which is a part of support structure 122 instead of impact surface 104. Similarly, in the retracting mode, when piston 132 is at the end of its reciprocal motion opposite impact surface 104 it strikes an interior wall of the piston cylinder which is part of support structure 122 instead of impact surface 102.

Figure 17:
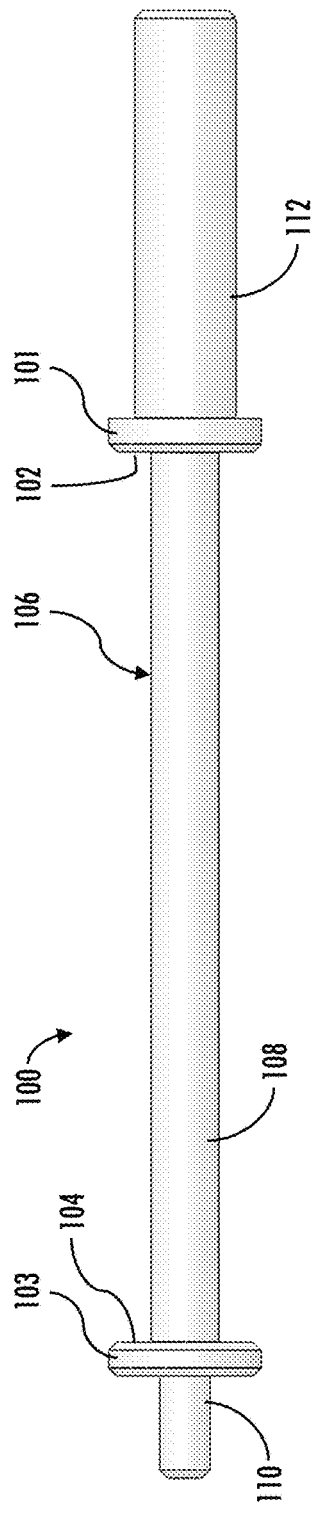
FIG. 17 is a side view of the hammer pin of the second embodiment.

Hammer pin 100 of the illustrated embodiment is shown in FIG. 17 and includes an elongate shaft 106 on which a first impact member 101 defining impact surface 102 and a second impact member 103 defining impact surface 104 are both secured. The shaft of hammer pin 100 includes a central shaft portion 108 separating the two impact members 101, 103, a shaft extension 110 and axially extending end portion 112. The shaft extension 110 has the smallest diameter of the three shaft portions while end portion 112 has the largest diameter of the three shaft portions.

Figure 22:
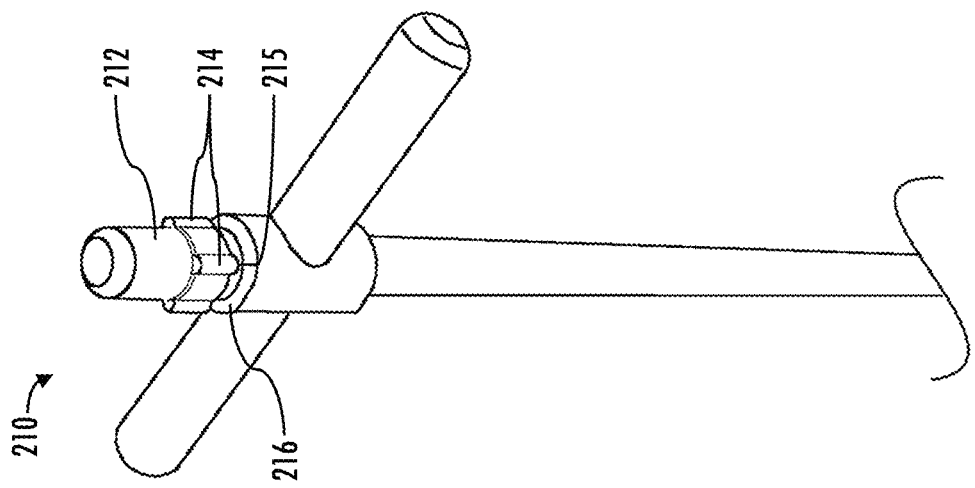
FIG. 22 is a partial perspective view of an example of an implant tool for use with the quick-release chuck of the second embodiment.
Figure 21:
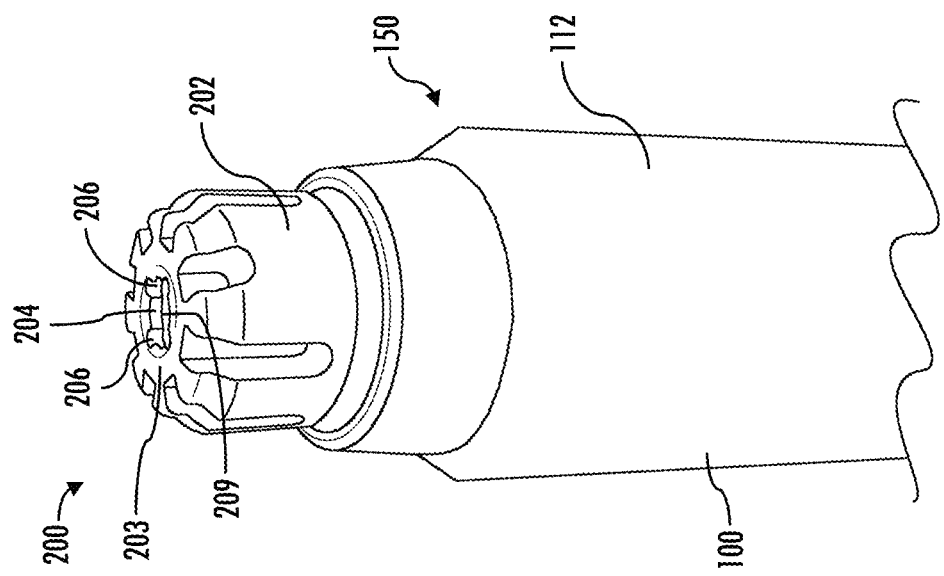
FIG. 21 is a perspective side view of the quick-release chuck of the second embodiment.
Figure 20:
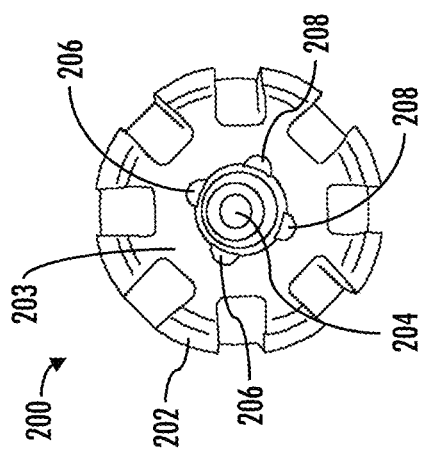
FIG. 20 is an end view of a quick-release chuck of the second embodiment.

End portion 112 of hammer pin 100 projects axially outwardly from support structure 122 and is adapted to be coupled with the object 48. In the illustrated embodiment, and as shown in FIGS. 20-22, a quick-release chuck 200 is disposed on the projecting end of hammer pin 100 to secure an object such as implant hardware, e.g., implant tool 210. In the illustrated embodiment, implant tool 210 has a stem 212 that is engageable with chuck 200 and an opposite end (not shown) that is detachably securable to an orthopedic implant whereby the tool may be used in the implantation or removal of the orthopedic implant.

Chuck 200 has a chuck body 202 which defines a chuck opening 204 for receiving stem 212 of tool 210. Chuck body 202 rotates relative to the central axis of opening 204 to secure or disengage tool 210. As can be seen in FIG. 20, chuck opening 204 defines four key ways 206 along the outer perimeter of chuck opening 204. Key ways 206 are shaped and positioned to receive keys 214 located on stem 212 of tool 210.

When chuck body 202 is in a first rotational position, key ways 206 are clear and keys 214 can be inserted therethrough whereby stem 212 can be fully seated in chuck opening 204. When chuck body 204 is subsequently rotated to a second position, a retention member 208 is moved into key way 206 and traps keys 214 within chuck body 202. Chuck body 202 may be spring biased toward this second locking position.

Chuck body 202 defines an axially facing strike surface 203 that is engaged with axially facing shoulder 216 of tool 210 when stem 212 is fully seated in chuck opening 204. Strike surface 203 imparts forceful impacts to shoulder 216 when the impactor is operated in the driving mode.

Retention members 208 are disposed between strike surface 203 and axially facing surfaces 215 of keys 214 when stem 212 is fully seated in chuck opening 204 and the chuck body is in the locked rotational position. This allows an axially facing pull surface 209 of the retention members 208 to impart forceful impacts to surfaces 215 when the impactor is operated in the retracting mode.

Chuck 200 is described herein as a quick-release chuck. The term "quick-release" in this context means that the chuck can be moved between positions allowing the insertion of stem 212 and securing stem 212 within the chuck body by manual manipulation of the chuck without requiring the use of a separate tool. Such chucks are also sometimes referred to as "keyless" chucks. A variety of other chucks, either quick-release or requiring the use of a separate tool, may also be employed with the impactors described herein. Such chucks are well-known in the art and may include chucks wherein a camming arrangement biases ball bearings radially inwardly to secure the inserted tool. It is noted that such chucks using ball bearings to secure a tool may employ the surfaces of the ball bearings as the strike and/or pull surfaces for imparting forceful impacts to the object. In other words, while it will often be advantageous, it is not necessary for the strike and pull surfaces to be planar surfaces. It is only necessary for at least one strike surface to face in a first axial direction away from the support structure (facing in a direction not necessarily parallel with the axial direction but at an angle of less than 90 degrees with the axis) and for at least one pull surface to face in an opposite second axial direction toward the support structure (facing in a direction not necessarily parallel with the axial direction but at an angle of less than 90 degrees with the axis). If a ball bearing were to form the strike and pull surfaces, it would be the one hemispherical side of the ball bearing that faces away from the support structure that would form the strike surface with the opposite hemispherical side of the ball bearing forming the pull surface.

Chuck 200 may be secured to the end of hammer pin 100 in any suitable manner. For example, chuck 200 may have a collar with an internal thread that engages an external thread on hammer pin 100 or a threaded shaft that engages a threaded bore on hammer pin 100. Chuck 200 may also be welded, secured using fasteners or otherwise engaged with hammer pin 100 in a manner that facilitates the transfer of axial forces between chuck 200 and hammer pin 100.

Alternatively, end portion 112 could be threaded so that a collar 61 with latches 60 may be secured on end portion 112 whereby pull surfaces on latches 60 may impart retracting forces to the object 48. The axial end surface of end portion 112 would form a strike surface 152 for imparting impact forces to the object 48. Alternative configurations of end portion 112 may also be employed to impart driving and pulling forces to object 48 as discussed above with regard to the embodiment of FIGS. 1-5.

Piston 132 includes three axially spaced piston heads 180, 182, 184 that divide the piston cylinder into four separate pressure chambers 179, 181, 183, 185. Piston 132 also defines an axially extending central opening 186. Central shaft portion 108 of hammer pin 100 extends through central opening 186 of piston 132 with piston 132 being reciprocatingly slidable on hammer pin 100. Impact surfaces 102, 104 are disposed on opposite axial ends of piston 132 and constrain the reciprocal motion of piston 132 on hammer pin 100.

When assembling pneumatic impactor 120, hammer pin 100 is advantageously formed out of two separate parts with central shaft portion 108 being inserted through opening 186 of piston 132 before securing the two parts of hammer pin 100 together. For example, impact member 103 could be a separate part that is secured to hammer pin 100 by welding or shaft extension 110 could be threaded with impact member 103 having a threaded bore whereby impact member 103 is secured to hammer pin 100 by threading impact member 103 onto shaft extension 110. Alternatively, central shaft portion 108 may be threaded at its end opposite impact member 103 with impact member 103 and shaft end portion 112 being a separate part with shaft end portion 112 having a threaded bore to receive the threaded end of central shaft portion 108. It is also noted that, in the illustrated embodiment, support structure 122 is formed out of two separate parts with the main body of support structure forming the central housing member 126 and a piston head member 133 being securable to member 126 whereby the piston 132 and hammer pin 100 can be installed in piston cylinder 131.

Impact surface 102 faces piston head 180 while impact surface 104 is disposed on the opposite axial end of piston 132 and faces piston head 184. The center piston head 182 is a solid cylindrical disk. The solid mass of central piston head 184 not only serves a purpose in dividing piston cylinder 131 into different pressure chambers, but also provides a significant mass which is beneficial in creating forceful impacts.

Figure 8:
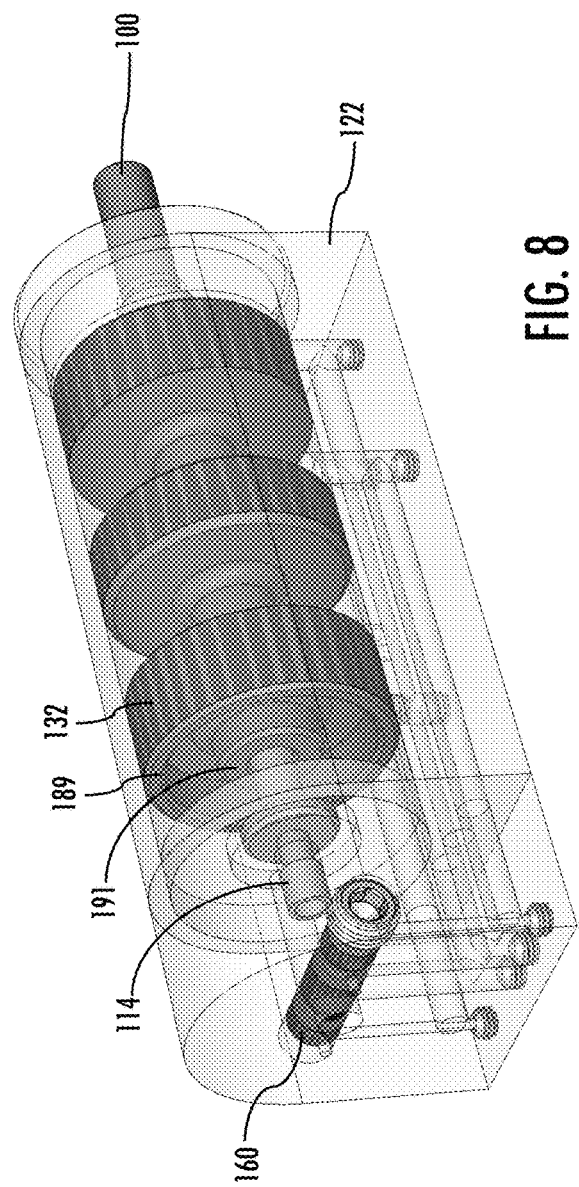
FIG. 8 is a transparent perspective view of the main body of the second embodiment.
Figure 9:
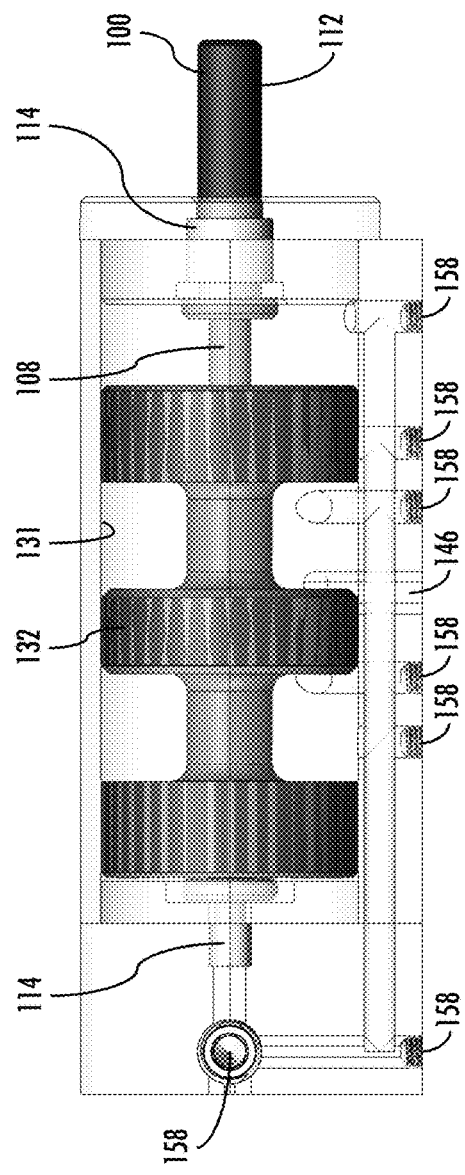
FIG. 9 is a transparent side view of the main body of the second embodiment.
Figure 10:
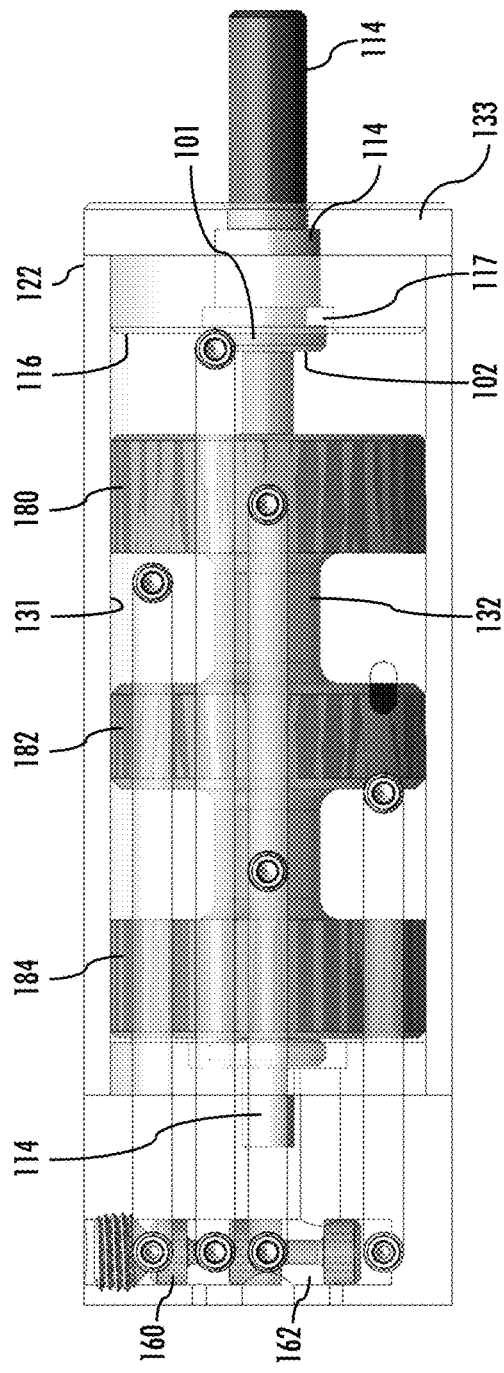
FIG. 10 is another transparent side view of the main body of the second embodiment with the piston in a first position.
Figure 11:
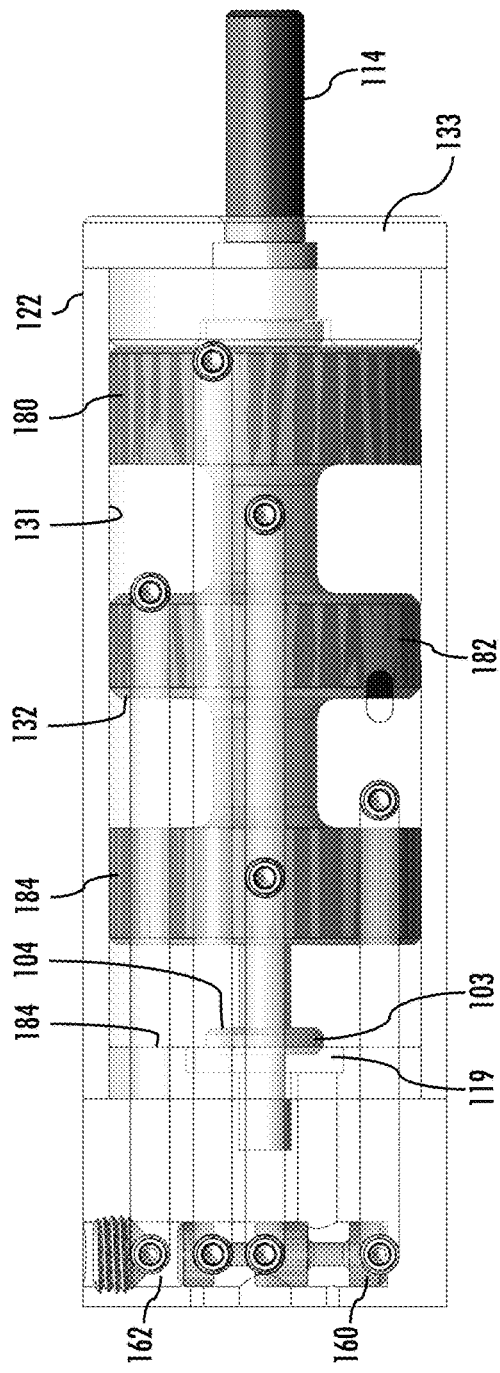
FIG. 11 is a transparent side view of the main body of the second embodiment similar to FIG. 10 but with the piston in a second position.
Figure 19:
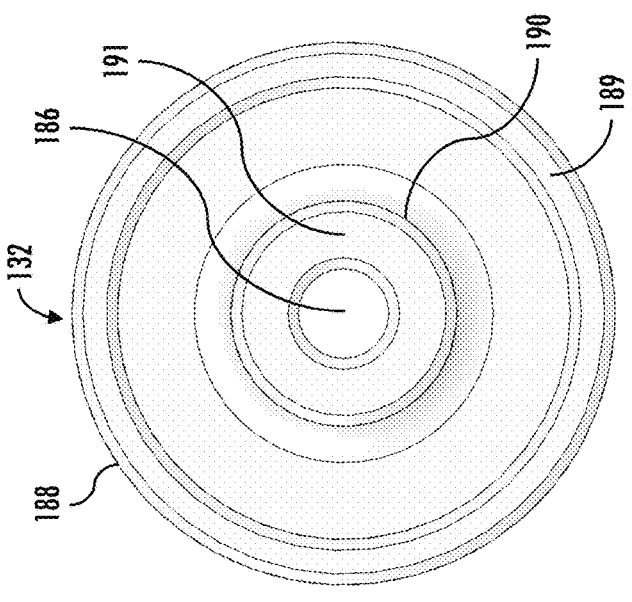
FIG. 19 is an end view of the piston of the second embodiment.
Figure 18:
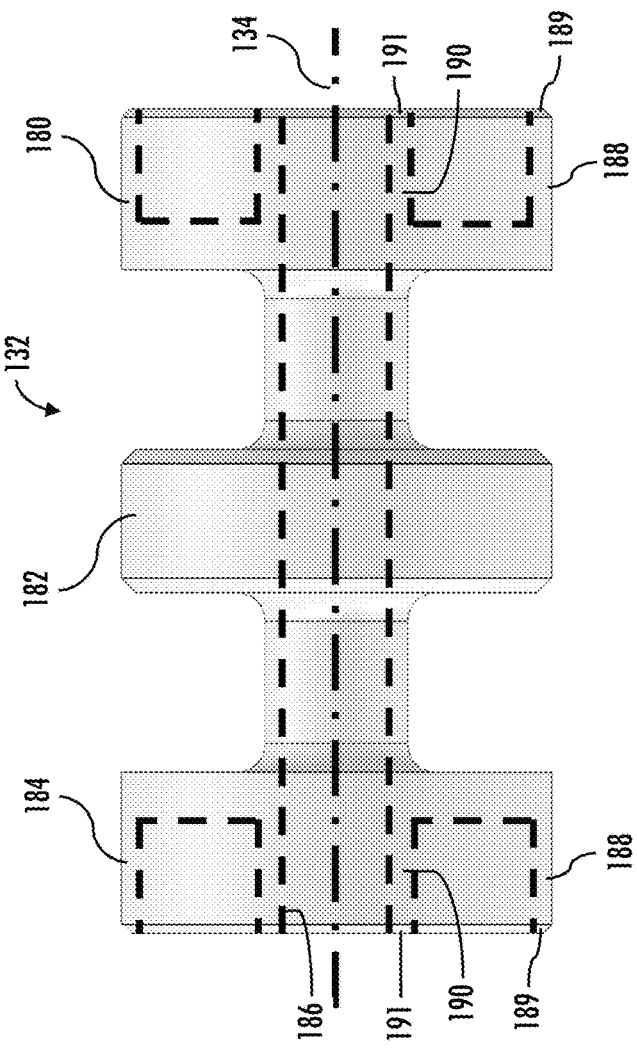
FIG. 18 is a side view of the piston of the second embodiment.

Piston heads 180 and 184 have a different configuration from central piston head 182 as best understood with reference to FIGS. 8, 18 and 19. Piston heads 180, 184 are each partially hollow, having a solid outer cylindrical wall 188 having a radially outer surface that mates with the interior cylindrical surface and an axially outwardly facing ring-shaped surface 189. An impact ring 190 surrounds central opening 186 and forms a ring-shaped axially outwardly facing contact surface 191. Impact ring 190 has a smaller diameter than the ring-shaped piston surface 189.

Hammer pin 100 is axially slidable relative to support structure 122. To facilitate this axial sliding motion, bushings 114 are mounted in support structure 122 at opposite axial ends of piston cylinder 131. One of the bushings 114 supports shaft extension 110 as can be seen in FIG. 8 while the second bushing supports end portion 112. The axial end faces 116, 118 of piston cylinder 131 each have a recess 117, 119. The recess 117 in axial end face 116 is shaped to receive impact member 101 of hammer pin 100 while the recess 119 in axial end face 118 is shaped to receive impact member 103 of hammer pin 100. Bushings 114 are advantageously formed out of a bronze material that will allow impactor 120 to be sterilized in an autoclave. The remaining parts of impactor 120 are advantageously formed out of a stainless steel material or other corrosion resistant metal material to facilitate the sterilization of impactor 120 in an autoclave. As discussed elsewhere, impactor 120 may include dampening washers and/or dampening sleeves 125 on grip members 124 which are formed out of a resiliently compressible material to absorb certain impact forces. The use of silicone to form such resiliently compressible parts will allow impactor 120 to be sterilized in an autoclave. A few drops of oil may be useful to provide lubrication for piston 132 and hammer pin 100 and such lubrication could be replenished after each sterilization of impactor 120.

The distance between axial end faces 116, 118 is such that hammer pin 100 can slide axially and only one of the impact members 101, 103 can be seated in its respective recess at any one time. When hammer pin 100 is slid toward axial end face 118, impact member 103 will be seated in recess 119. When piston 132 reciprocatingly moves while hammer pin 100 is in this position, contact surface 191 of piston head 180 will impact impact surface 102 of impact member 101 at one end of the piston's reciprocal motion and piston surface 189 of piston head 184 will impact axial end face 118 at the opposite end of the piston's reciprocal motion. This will place impactor 120 in its driving mode. Impactor 120 is in the driving mode in FIG. 10.

In the driving mode, when piston head 180 strikes impact surface 102, a force will be transmitted to an object 48 coupled to end portion 112 of hammer pin 100 in an axial direction directed away from support structure 122. When piston head 184 strikes axial end surface 118, the force will be transmitted to support structure 122 being held by a user. The user will thereby absorb this force. The support structure 122 will also have the ability to move a small distance away from object 48 under the impact of this force before imparting any retracting force on object 48. A dampening member may be used to form axial end surface 118 or be coupled with axial end surface 118 to assist the user in resisting such forces as further discussed below. This relative movement of support structure 122 will also absorb some of this impact force in the retracting direction. The user will then simply move the support structure 122 relative to hammer pin 100 in a direction toward object 48 before the next driving impact occurs to maintain the impactor 120 in its driving mode configuration.

When hammer pin 100 is slid toward axial end face 116, impact member 101 will be seated in recess 117. When piston 132 reciprocatingly moves while hammer pin 100 is in this position, contact surface 191 of piston head 184 will impact impact surface 103 of impact member 104 at one end of the piston's reciprocal motion and piston surface 189 of piston head 180 will impact axial end face 116 at the opposite end of the piston's reciprocal motion. This will place impactor 120 in its retracting mode. Impactor 120 is in the retracting mode in FIG. 11.

In the retracting mode, when piston head 184 strikes impact surface 104, a force will be transmitted to an object 48 coupled to end portion 112 of hammer pin 100 in an axial direction directed towards support structure 122. When piston head 180 strikes axial end surface 116, the force will be transmitted to support structure 122 being held by a user. The user will thereby absorb this force. The support structure 122 will also have the ability to move a small distance toward object 48 under the impact of this force before imparting any driving force on object 48. This relative movement of support structure 122 will also absorb some of this impact force in the driving direction. A dampening member may be used to form axial end surface 118 or be coupled with axial end surface 118 to assist the user in resisting such forces as further discussed below. The user will then simply move the support structure 122 relative to hammer pin 100 in a direction away from object 48 before the next retracting impact occurs to maintain the impactor 120 in its retracting mode configuration.

To initially place impactor 120 into either the driving mode or the retracting mode, the user can simply grasp projecting end portion 112 and either push hammer pin 100 into support structure 122 to place the impactor 120 into the driving mode, or, pull hammer pin 100 out of support structure 122 to place impactor 120 into the retracting mode. Alternatively, end portion 112 can first be coupled to the object 48 and, to place the impactor in the driving mode, the user would move the support structure 122 relative to hammer pin 100 by pushing it towards object 48, and, to place the impactor in the retracting mode, the user would move the support structure 122 relative to hammer pin 100 by pulling it away from object 48.

During use, the user will maintain a pressure on the support structure 122 pushing it towards object 48 when the impactor 120 is in the driving mode. This pressure exerted by the user will absorb the forces generated in the retracting direction and also maintain the impactor 120 in the driving mode. Similarly, if using the impactor 120 in the retracting mode, the user will maintain a pressure on support structure 122 pulling it away from object 48. This pulling force exerted by the user will absorb forces generated in the driving direction and also maintain the impactor in the retracting mode. Dampening members forming or coupled with axial end surfaces 116, 118 may also be employed to absorb forces and thereby lessen the peak forces that must be absorbed by the user. Similarly, dampening members coupled with grip members 124 may also be employed to lessen the peak forces absorbed by the user.

While the illustrated impactor 120 allows hammer pin 100 to axially move relative to support structure 122 at all times, a locking mechanism may optionally be employed to maintain hammer pin 100 in a fixed relative axial position to selectively and securely maintain hammer pin 100 in either a driving or retracting mode position. For example, one or more locking pins mounted on support structure 122 could be used to selectively engage or disengage from one or more recesses or bores in hammer pin 100 to secure hammer pin 100 at a desired axial position within support structure 122 to thereby securely maintain hammer pin 100 in either the driving mode or retracting mode. Alternative methods of securing hammer pin 100 in the desired axial position may also be employed. For example, the selective movement of one or more magnetic members could be employed to hold hammer pin 100 in a desired axial position. The use of such a magnetic retention mechanism would also allow for the movement of hammer pin 100 if a sufficiently large axial force were applied to the hammer pin. The ability to define such a predetermined break-away force could be beneficial in some applications.

In the illustrated embodiment, surfaces 189, 191 lie in the same plane and impact members 101, 103 can be fully seated in their respective recesses 117, 119. However, alternative configurations may also be employed. For example, opposing piston surfaces 189 might be positioned at a greater axial distance from each other than contact surfaces 191, in which case recesses 117, 119 would not have to fully seat impact members 101, 103 to before the respective piston surface impacted the axial end surface of the piston cylinder.

As mentioned above, some embodiments may employ dampening members. For example, a resiliently compressible material on either the axially facing piston cylinder surfaces 116, 118 or to form the ring surfaces 189 of piston heads 180, 184 to absorb the impact forces generated by piston 132 that are directed in the opposite direction than the driving or retracting forces being imparted to object 48 by the reciprocal motion of piston 132 could be used to form such dampening members. For example, silicone washers could be installed at these locations for purposes of absorbing such oppositely directed impact forces. A sleeve 125 of resiliently deformable padding material may also be installed on grip members 124 to absorb impact forces. Appropriately configured spring arrangements and other force dampening materials or components could also be employed as dampening members.

Pressure control system 136 is used to move piston 132 in a reciprocating motion. Pressure control system 136 is adapted to be connected to a supply of pressurized gas such as the pressurized air typically found in operating rooms. The air supply is provided to control system 136 through inlet passage 138 formed in support structure 122. Inlet passage 138 may be a threaded bore whereby a connector or valve assembly may be attached to support structure 122 and an attachment point for coupling impactor 120 with the pressurized air supply. For example, a pressure regulating valve that allows the user to control the pressure of the gas acting on piston 132 could be attached at inlet passage 138 to couple impactor 122 to the supply of pressurized gas as further discussed below with reference to FIG. 23.

Inlet passage 138 supplies the pressurized gas to spool cylinder 162. A control spool 160 is slidingly disposed in spool cylinder 162. Control spool 160 includes three axially spaced spool heads 164, 166, 168 which sealingly engage the interior surface of spool cylinder 162 and divide spool cylinder 162 into four separate pressure chambers 163, 165, 167, 169. Control spool 160 controls the supply of pressurized gas to piston cylinder 131 to thereby generate reciprocating movement of the piston. It is noted that the separate piston chambers 179, 181, 183, 185 and separate spool chambers 163, 165, 167, 169 do not have fixed positions within piston cylinder 131 and control spool cylinder 162 but are defined by the position of the piston 132 or control spool 160 within their respective cylinders. For example, piston chamber 183 is the space between piston heads 182 and 184 regardless of where piston 132 is positioned within piston cylinder 131 and spool chamber 165 is the space between spool heads 164 and 166 regardless of where control spool 160 is located within spool cylinder 162.

The operation of pressure control system 136 is best understood with reference to FIGS. 10A, 11A, 12 and 13. In FIGS. 10A and 11A, the black arrows and cylinder chambers that are blacked out are being supplied with pressurized gas while the white arrows indicate volumes which are being vented to the ambient environment and thus are at a lower pressure than those volumes being supplied with pressurized gas. During operation of pressure control system 136, piston 132 and control spool 160 will reciprocate in their respective cylinders in a coordinated fashion.

Control spool cylinder 162 is in communication with piston cylinder 131 via four separate passages 139, 140, 141 and 142. Each of the passages 139, 140, 141 and 142 has an axially extending middle portion and two end portions that extend perpendicular to the middle portion, one end portion provides communication to the spool cylinder and the other end portion provides communication to the piston cylinder. Passage 140 also has a third perpendicular passage that provides communication to the piston cylinder 131. Passage 143 provides communication between spool cylinder 162 and recess 119. With regard to passage 140 which has two separate branches in communication with piston cylinder 131 at axially spaced apart locations, it is noted that either piston head 180 or piston head 184 will block one of the branch lines from communicating with piston cylinder 131. As piston 132 moves, one of the branch lines will begin to be exposed and the other will simultaneously begin to be closed in an alternating manner as piston 132 reciprocates.

Figure 12:
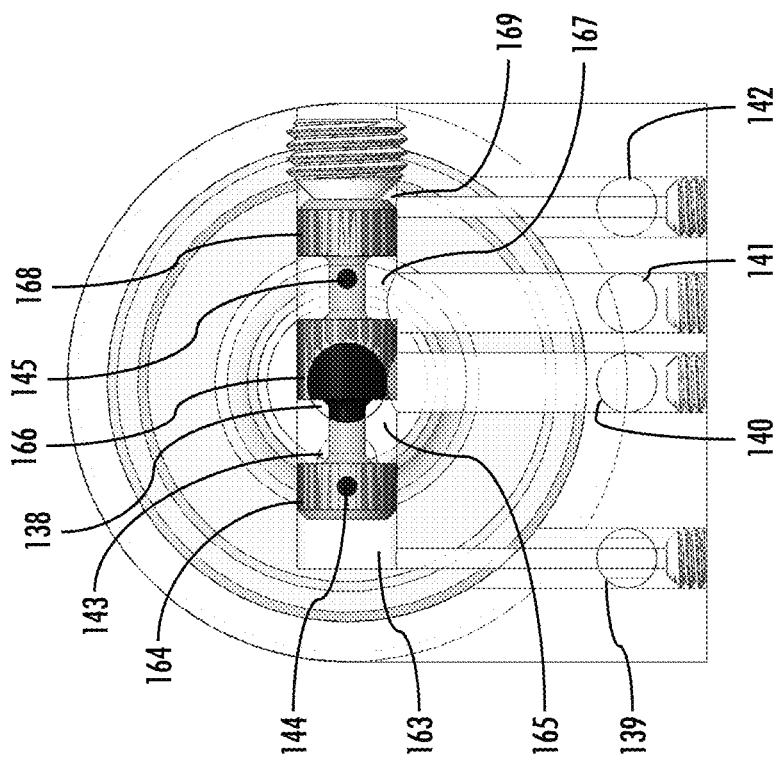
FIG. 12 is a transparent end view of the main body of the second embodiment showing the control spool in a first position.
Figure 16:
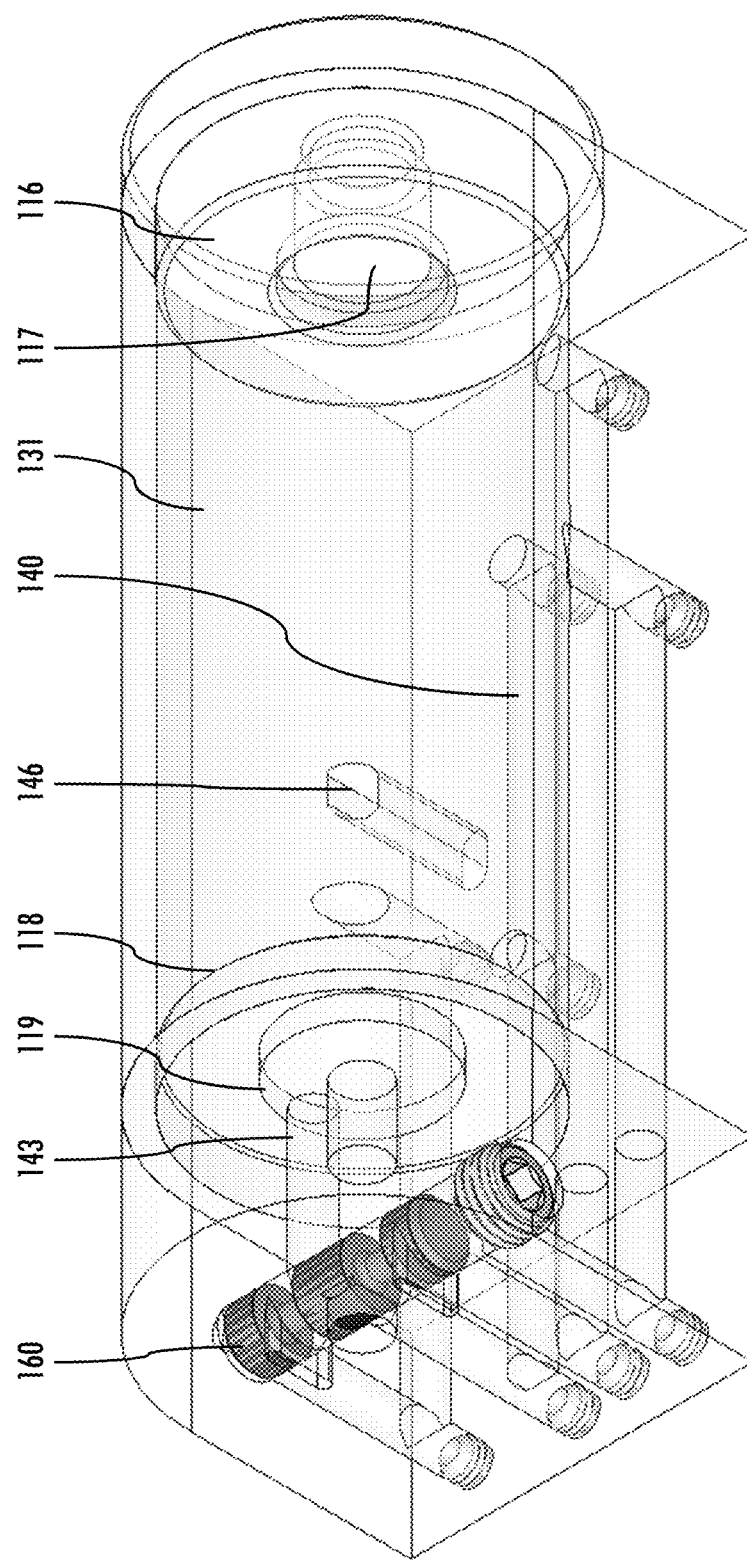
FIG. 16 is a transparent perspective view of the main body of FIG. 14 with the piston and hammer pin removed.

FIG. 10A shows piston 132 at a position proximate axial end surface 118. FIG. 12 is an end view showing control spool 160 in the same position as in FIG. 10A. In this position shown in FIGS. 10A and 12, pressurized gas is communicated from inlet passage 138 to spool cylinder chamber 165. From spool cylinder chamber 165 passage 140 communicates the pressurized gas to piston chamber 183 and pressurized gas in chamber 183 is then communicated through passage 142 to spool cylinder chamber 163. Piston head 180 blocks communication between piston cylinder 131 and one of the branch lines of passage 140. Pressurized gas in spool cylinder chamber 165 is also communicated through passage 143 to recess 119. Piston chamber 181 is vented to the atmosphere through piston vent passage 146. Spool chamber 169 is in communication with piston chamber 181 through passage 142 and is therefore also vented to the atmosphere through passage 181, piston chamber 181 and piston vent 146. Spool chamber 167 is vented to the atmosphere through spool vent 145. Spool head 164 blocks the venting of any gas from spool cylinder 162 through vent passage 144. Piston chamber 170 is vented through the atmosphere through passage 141, spool chamber 167 and spool vent passage 145.

Thus, in FIGS. 10A and 12, with piston 132 located in a proximal portion of the piston cylinder 131, pressurized air will present in the two most proximal piston chambers 185, 183 and the two most distal piston chambers 179, 181 will be vented to the atmosphere. As a result, piston 132 will be biased by the air pressure towards axial end surface 116. In spool cylinder 162, spool chambers 163 and 165 will be subject to pressurized air and spool chambers 167, 169 will be vented to the atmosphere. As a result, pressurized air within spool cylinder 162 will bias control spool 160 from the position depicted in FIGS. 10A and 12 toward the position shown in FIGS. 11A and 13.

Figure 13:
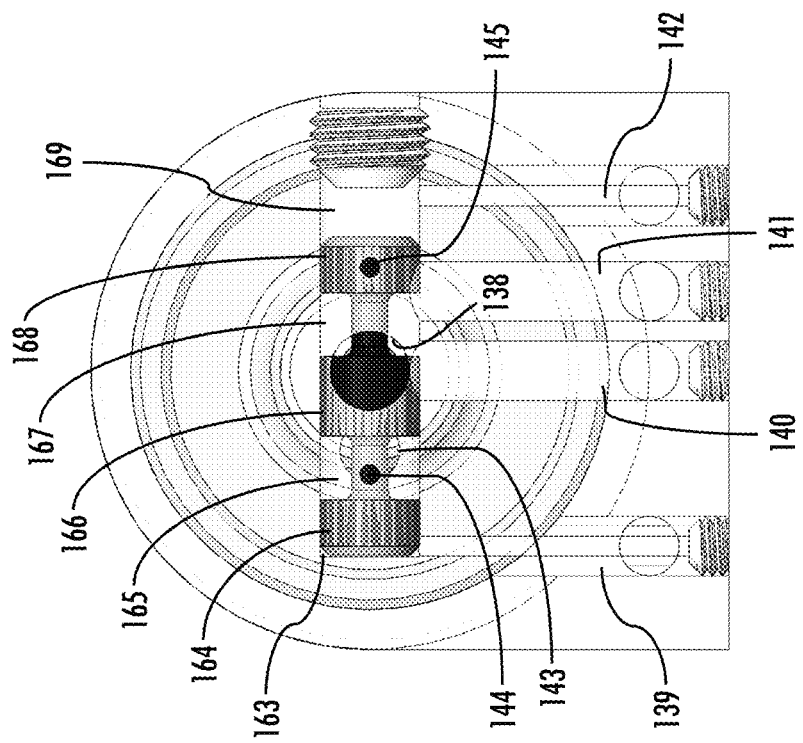
FIG. 13 is a transparent end view of the main body of the second embodiment showing the control spool in a second position.

As piston 132 and control spool 160 move within their respective cylinders from the positions shown in FIGS. 10A and 12 toward the positions shown in FIGS. 11A and 13, the pathways by which pressurized air is introduced into the spool cylinder 162 and piston cylinder 131 and which spool and piston chambers are vented to the atmosphere will change and the air pressure will no longer continue to bias control spool 160 and piston 132 in the same directions. The changes in air pressure within the separate chambers within spool cylinder 162 and piston cylinder 131 will take a small increment of time to occur and the momentum of spool 160 and piston 132 will carry them to the positions shown in FIGS. 11A and 13 where piston 132 will impact either an impact surface or an axial end surface.

When piston 132 and control spool 160 reach the positions shown in FIGS. 11A and 13, inlet passage 138 will be communicating pressurized air into spool chamber 167 from which it will be communicated into passages 140 and 141. Movement of piston 132 to the position of FIG. 11A results in piston head 180 uncovering one of the branch lines of passage 140 and piston head 184 covering the other branch line of passage 140. As a result, pressurized air is communicated through passage 140 to piston chamber 181 from where it is also communicated to passage 142 and then to spool chamber 169. Pressurized air communicated from spool chamber 167 to passage 141 is communicated to piston chamber 179. Piston chamber 183 is vented to the atmosphere through piston vent 146 and spool chamber 163 is also vented to the atmosphere through piston vent 146 because spool chamber is in communication with piston chamber 183 through passage 139. Piston chamber 185 is vented to the atmosphere through passage 143 which is in communication with spool vent 144 through spool chamber 165. Spool vent 145 is blocked from venting spool cylinder 162 by spool head 168.

Thus, in the positions shown in FIGS. 11A and 13, piston chambers 179, 181 are subject to pressurized air and piston chambers 183, 185 are vented to the atmosphere while spool chambers 167, 169 are subject to pressurized air and spool chambers 163, 165 are vented to the atmosphere. This will cause piston 132 to move back towards the position shown in FIG. 10A and control spool 160 to move back the position shown in FIGS. 10A and 12. Once the spool and piston return to the positions of FIGS. 10A and 12 the cycle will repeat itself. This cyclical movement of the piston and control spool will continue until the supply of pressurized gas through inlet passage 138 is terminated.

In the illustrated embodiment, the spool heads and piston heads have a beveled outer perimeter to prevent the chambers at the axial ends of the control cylinder and piston cylinder from being completely eliminated when the control spool and piston are at the limits of their axial movement.

It is also noted that FIG. 10A shows hammer pin 100 in the driving mode and FIG. 11A shows hammer pin 100 in the retracting mode. The passage openings into piston cylinder 131 are sized such that the principles of operation of the pressure control system 136 discussed above are applicable in both the driving mode and retracting mode for the full range of reciprocal motion.

It is further noted that in the illustrated embodiment, the passages that are part of pressure control system 136 are efficiently manufactured by drilling passages into support structure 122. For those passages that are not vented to the atmosphere, threaded caps 158 are installed in the passages to seal the passages. Other methods of manufacture and/or sealing of passages may alternatively be used.

Figure 23:
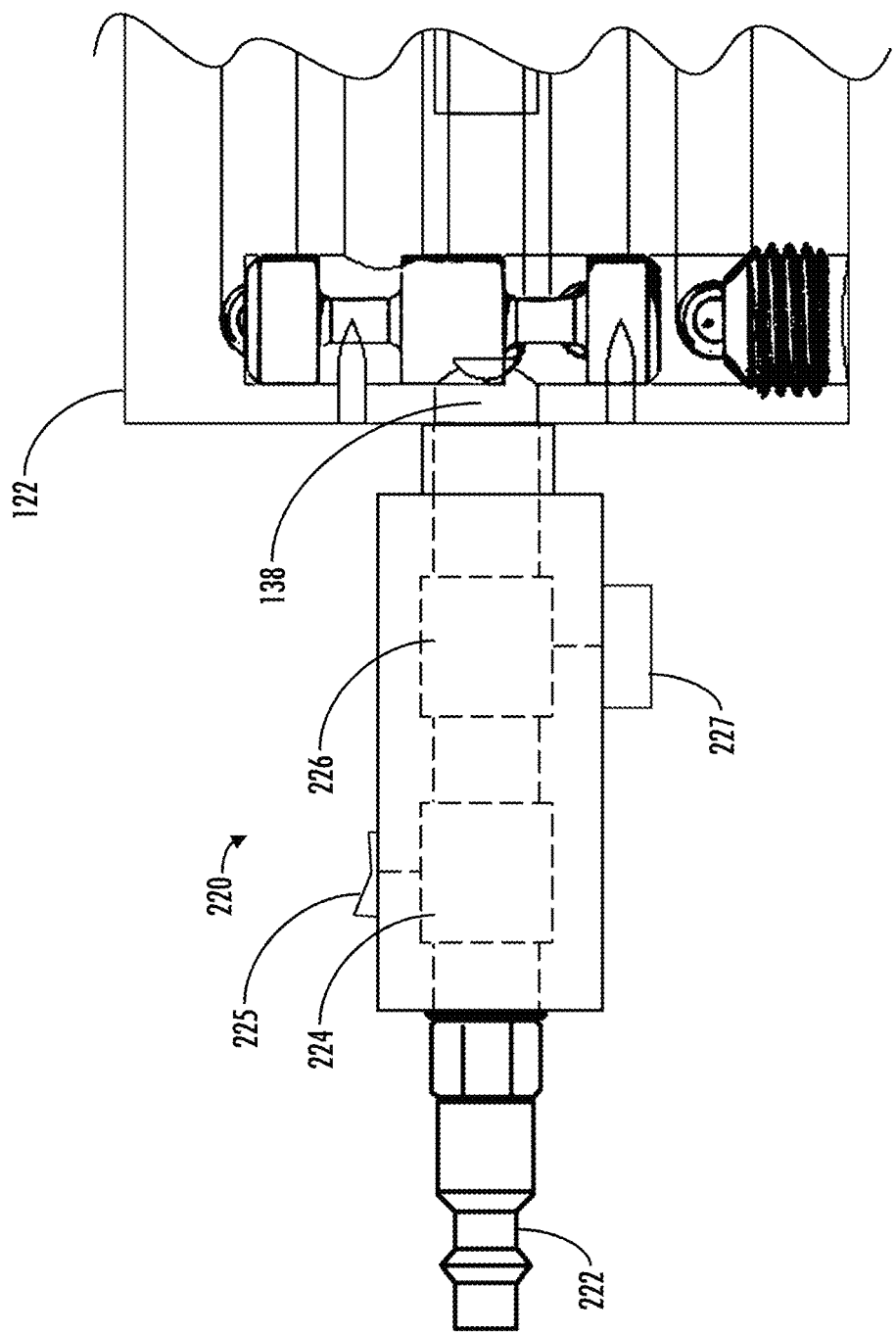
FIG. 23 is a schematic representation of a valve assembly for the second embodiment.
Figure 24:
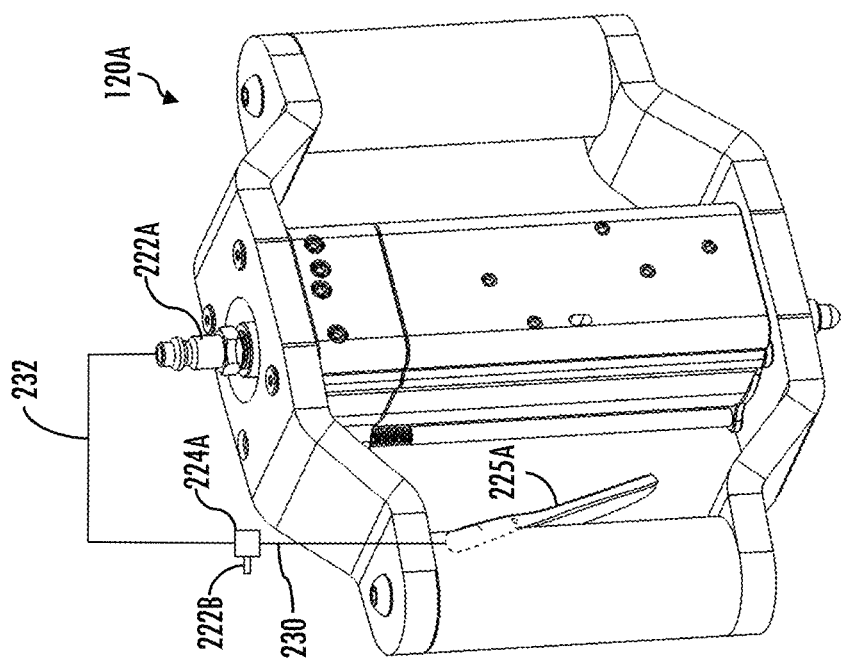
FIG. 24 is a representation of a modified version of the second embodiment.

Pressure control system 136 may also include a valve assembly 220 as schematically depicted in FIG. 23. Valve assembly 220 shown in FIG. 23 is detachably securable to support structure 122, however, a valve assembly mounted within support structure 122 may also be employed. Valve assembly 220 has a threaded stem that engages a threaded bore formed by inlet passage 138 to sealingly and securely attach valve assembly 220 to support structure, however, other suitable methods may also be employed.

Valve assembly 220 includes a connector 222 for connecting with a source of pressurized gas such as the pressurized air supply typically found in operating rooms. An internal passage communicated pressurized gas from connector 222 to shut-off valve 224. A user-operable actuator 225 allows the user to open and close shut-off valve 224 to thereby allow or terminate the flow of pressurized gas to inlet passage 138. Disposed between shut-off valve 224 and inlet passage 138 is a pressure regulating valve 226 that can be used to vary the pressure of the gas communicated from the gas supply to inlet passage 138. A user-operable control 227 allows the user to adjust valve 226 and thereby control the pressure of the gas entering inlet passage 138. Various alternative embodiments of valve assembly 220 are also possible. For example, the shut-off valve and pressure regulating valve could be replaced by a single valve that performs both functions and has only a single user-operable control. Either of the valves could also be omitted entirely, however, it will generally be desirable for the impactor to include a valve having a user-operable control that allows the supply of pressurized gas to inlet passage 138 to be cut-off. It would be possible, however, to omit valves 224 and/or 226 and instead rely on a cut-off valve integral with the pressurized gas supply and/or a pressure regulating valve integral with the pressurized gas supply to perform the same functions as one or both of valves 224, 226.

FIGS. 24 and 25 show a modified version of the second embodiment of the impactor. Impactor 120A shown in FIGS. 24 and 25 functions in the same manner as impactor 120 but has a construction that differs. More specifically, many of the individual parts of impactor 120 correspond to an assembly of smaller parts in impactor 120A or single parts of impactor 120A correspond to an assembly of parts in impactor 120.

As shown in FIGS. 24 and 25, impactor 120A has a connector 222A mounted on the support structure in direct communication with the inlet passage 138A. Impactor 120A also has a user-operable actuator 225A for actuating a cut-off valve 224A to thereby terminate or allow the entry of pressurized gas into connector 222A. As can be seen in FIGS. 24 and 25, actuator 225A is positioned on one of the grip members whereby the user of impactor 120A can easily open and close the cut-off valve to allow or terminate the flow of pressurized gas into connector 222A and the inlet passage 138A.

FIG. 24 schematically depicts the arrangement between actuator 225A, cut-off valve 224A. When using this arrangement, pressurized gas will be connected to impactor 120A at connector 222B so that cut-off valve 224A will be positioned between the supply of pressurized gas and inlet passage 138A. Pressure line 232 communicated pressurized gas from cut-off valve 224A to connector 222A. Line 232 may take the form of a short external flexible hose that has a male connector for mating with connector 222A. Alternatively, line 232 could be permanently connected with inlet passage 138A and connector 222A omitted.

Linkage 230 connects actuator 225A with valve 224A to open and close valve 224A and thereby allow or prevent the passage of pressurized gas. Linkage 230 may be a mechanical linkage whereby it transmits mechanical forces from actuator 225A to valve 224A to open and close valve 224A. Alternatively, valve 224A may be an electrically controlled/actuated valve with user-operable actuator 225A generating an electrical signal that is communicated to valve 224A via linkage 230, with linkage 230 taking the form of an insulated copper wire or other suitable means for communicating an electrical signal. Valve 224A would have an integral electrically powered actuator that would then open or close the valve in response to the signal generated by actuator 225A. A battery or other source of electrical power would be supplied for powering the valve and generating the electrical signal. Various other configurations may also be employed.

Valve 224A and connector 222B may be part of a valve assembly mounted on the upper portion of one of the grip arms, formed integrally with the support structure of impactor 120A or otherwise mounted on impactor 120A.

While this invention has been described as having an exemplary design, the present invention may be further modified within the spirit and scope of this disclosure. This application is therefore intended to cover any variations, uses, or adaptations of the invention using its general principles.

What is claimed is:

1. A bi-directional pneumatic impactor for imparting impact forces to an object comprising:
    a support structure defining a piston cylinder and at least one grip member whereby a user can manually grasp the support structure;
    a piston reciprocally moveable along a piston axis within the piston cylinder;
    a pressure control system coupled with the piston cylinder and adapted to be connected to a supply of pressurized gas, wherein the pressure control system is adapted to reciprocatingly move the piston along the piston axis;
    an impact transfer assembly disposed on the support structure and adapted to be coupled with the object whereby the impact transfer assembly transfers impact forces generated by the piston to the object;
    wherein the pneumatic impactor is selectively switchable between a driving mode and a retracting mode wherein, in the driving mode, the piston generates forceful impacts at a first end of the reciprocal movement and the impact transfer assembly transfers impact forces generated at the first end of the reciprocal movement to the object; and, in the retracting mode, the piston generates forceful impacts at a second end of the reciprocal movement opposite the first end and the impact transfer assembly transfers impact forces generated at the second end of the reciprocal movement to the object, and
    wherein the pneumatic impactor is selectively switchable between the driving mode and the retracting mode by selectively configuring the impact transfer assembly and wherein the impact transfer assembly includes an elongate hammer pin, the hammer pin being axially moveable relative to the piston and the support structure, the hammer pin including;
        an axially extending end projecting from the support structure and adapted to be coupled with the object; and
        first and second impact surfaces wherein the first and second impact surfaces face in opposite axial directions and the piston is engageable with the first impact surface to impart impact forces to the hammer pin in a first axial direction and the piston is engageable with the second impact surface to impart impact forces to the hammer pin in an opposite second axial direction and wherein the hammer pin is axially movable relative to the housing between a first axial position wherein only the first impact surface of the first and second impact surfaces is engageable by the piston and a second axial position wherein only the second impact surface of the first and second impact surfaces is engageable by the piston.

2. The pneumatic impactor of claim 1 wherein the at least one grip member comprises first and second grip members and wherein the piston axis is symmetrically disposed between the first and second grip members.

3. The pneumatic impactor of claim 2 wherein the piston is disposed in an elongate central housing member of the support structure, the elongate central housing member extending parallel with the piston axis between first and second opposing ends of the central housing member and wherein the first and second grip members are disposed on opposite sides of the central housing member and are axially positioned between the first and second opposing ends of the central member.

4. The pneumatic impactor of claim 1 further comprising a user-adjustable pressure regulating valve that adjusts the pressure of the gas acting on the piston.

5. The pneumatic impactor of claim 1 wherein the impact transfer assembly includes at least one strike surface and at least one pull surface wherein the at least one strike surface faces in a first axial direction and the at least one pull surface faces in a second axial direction opposite the first axial direction.

6. The pneumatic impactor of claim 5 wherein the impact transfer assembly includes a quick-release chuck and the at least one strike surface and the at least one pull surface are defined by the chuck.

7. The pneumatic impactor of claim 5 wherein the at least one strike surface is defined by a strike member, the strike surface forming a planar surface intersecting the piston axis at a perpendicular angle, and wherein the impact transfer assembly further comprises a plurality of latches circumferentially and symmetrically disposed about the strike surface, the at least one pull surface comprising a plurality of pull surfaces with each of the plurality of latches defining one of the plurality of pull surfaces and wherein each of the plurality of latches is moveable between an unengaged position and an engaged position wherein, when the plurality of latches are in the unengaged position, the plurality of latches allow the object to be engaged with the strike surface and, when the plurality of latches are in the engaged position with the object engaged with the strike surface, each of the plurality of latches engage the object with a corresponding one of the plurality of pull surfaces to thereby secure the object between the strike member and the plurality of latches.

8. The pneumatic impactor of claim 1, wherein the piston defines an axially extending central opening, and wherein the elongate hammer pin extends through the central opening of the piston, the piston being reciprocatingly slidable on the hammer pin, the first and second impact surfaces of the hammer pin being disposed on opposite first and second axial ends of the piston.

9. The pneumatic impactor of claim 1, at the first axial end of the piston, the piston defines a first axially outwardly facing contact surface engageable with the first impact surface when the hammer pin is in the first axial position and a first axially outwardly facing piston surface is engageable with the support structure when the hammer pin is in the second axial position, and, at the second axial end of the piston, the piston defines a second axially outwardly facing contact surface engageable with the second impact surface when the hammer pin is in the second axial position and a second axially outwardly facing piston surface engageable with the support structure when the hammer pin is in the first axial position.

10. The pneumatic impactor of claim 1, wherein the pressure control system includes a control spool slidably disposed in a spool cylinder, the control spool controlling the supply of pressurized gas to the piston cylinder to thereby generate reciprocating movement of the piston.

11. The pneumatic impactor of claim 10 wherein the piston includes three axially spaced piston heads which divide the piston cylinder into four separate pressure chambers, the piston cylinder defining at least one piston vent passage and wherein at least one spool vent passage is in communication with the spool cylinder and wherein, in a first piston position wherein the piston is disposed in a proximal portion of the piston cylinder and the spool is disposed in a first spool position within the spool cylinder, the two most proximal piston chambers are supplied with pressurized gas and the two most distal piston chambers are vented to the atmosphere through the at least one piston vent passage and the at least one spool vent passage and pressurized air within the spool cylinder biasing the spool toward a second spool position, and, in a second piston position wherein the piston is disposed in a distal portion of the piston cylinder and the spool positioned in a second spool position, the two most distal piston chambers are supplied with pressurized gas and the two most proximal piston chambers are vented to the atmosphere through the at least one piston vent passage and the at least one spool vent passage and pressurized air within the spool cylinder biasing the spool toward the first spool position.

12. The pneumatic impactor of claim 11 wherein the at least one spool vent passage takes the form of two spool vent passages and the spool blocks the venting of air through one of the spool vent passages in the first spool position and blocks the venting of air through the other one of the spool vent passages in the second spool position.

13. The pneumatic impactor of claim 12 wherein, at the first axial end of the piston, the piston defines a first axially outwardly facing contact surface engageable with the first impact surface when the hammer pin is in the first axial position and a first axially outwardly facing piston surface is engageable with the support structure when the hammer pin is in the second axial position, and, at the second axial end of the piston, the piston defines a second axially outwardly facing contact surface engageable with the second impact surface when the hammer pin is in the second axial position and a second axially outwardly facing piston surface engageable with the support structure when the hammer pin is in the first axial position.

14. A bi-directional pneumatic impactor for imparting impact forces to an object, comprising:
 a support structure having at least one grip member whereby a user can manually grasp the support structure;
 an elongated piston cylinder defined in said support structure and having axially opposite first and second end faces, said first and second end faces defining respective first and second contact surfaces;
 an elongated hammer pin slidably disposed within said piston cylinder, said hammer pin having;
  an end portion projecting outside said piston cylinder for imparting the impact forces to the object;
  a first impact member arranged inside said piston cylinder adjacent said first end face, said first impact member defining a first impact surface; and
  a second impact member arranged inside said piston cylinder adjacent said second end face, said second impact member defining a second impact surface;
 a piston slidably concentrically disposed on said hammer pin and moveable along a piston axis within the piston cylinder between said first and second impact members of said hammer pin, said piston selectively engageable with said first and second impact members to impart the impact forces to said first and second impact surfaces of said hammer pin; and
 a pressure control system coupled with the piston cylinder and adapted to be connected to a supply of pressurized gas, wherein the pressure control system is configured to apply pressurized gas to the piston to reciprocate the piston within the piston cylinder,
 wherein when the second impact member is engaged to said second contact surface, the piston reciprocates between engaging said second end face and engaging said first impact surface to impart the impact forces in a first direction to said hammer pin,
 wherein when the first impact member is engaged to said first contact surface, the piston reciprocates between engaging said first end face and engaging said second impact surface to impart the impact forces in a second direction to said hammer pin that is opposite said first direction, and
 wherein said end portion of said elongated hammer pin is configured to be coupled to the object and said elongated hammer pin is configured to be manually selectively positioned with the first impact member engaged to said first contact surface, to impart the impact forces to the object in the first direction, and with the second impact member engaged to said second contact surface, to impart the impact forces to the object in the second direction.

15. The bi-directional pneumatic impactor of claim 14, wherein said first and second end faces each define a recess sized to receive a corresponding one of the first and second impact members, each recess defining the corresponding first and second contact surface.

16. The bi-directional pneumatic impactor of claim 14, wherein the elongated hammer pin is manually selectively positioned by moving the support structure toward the object to impart the impact forces in the first direction, and moving the support structure away from the object to impart the impact forces in the opposite second direction.

17. The bi-directional pneumatic impactor of claim 14, further comprising dampening members disposed at said first and second end faces of said piston cylinder.

18. The pneumatic impactor of claim 14, wherein the pressure control system includes a control spool slidably disposed in a spool cylinder, the control spool controlling the supply of pressurized gas to the piston cylinder to thereby generate reciprocating movement of the piston.

19. The pneumatic impactor of claim 18, wherein the piston includes three axially spaced piston heads which divide the piston cylinder into four separate pressure chambers, the piston cylinder defining at least one piston vent passage and wherein at least one spool vent passage is in communication with the spool cylinder and wherein, in a first piston position wherein the piston is disposed in a proximal portion of the piston cylinder and the spool is disposed in a first spool position within the spool cylinder, the two most proximal piston chambers are supplied with pressurized gas and the two most distal piston chambers are vented to the atmosphere through the at least one piston vent passage and the at least one spool vent passage and pressurized air within the spool cylinder biasing the spool toward a second spool position, and, in a second piston position wherein the piston is disposed in a distal portion of the piston cylinder and the spool positioned in a second spool position, the two most distal piston chambers are supplied with pressurized gas and the two most proximal piston chambers are vented to the atmosphere through the at least one piston vent passage and the at least one spool vent passage and pressurized air within the spool cylinder biasing the spool toward the first spool position.

20. The pneumatic impactor of claim 19 wherein the at least one spool vent passage takes the form of two spool vent passages and the spool blocks the venting of air through one of the spool vent passages in the first spool position and blocks the venting of air through the other one of the spool vent passages in the second spool position.

21. The pneumatic impactor of claim 15, wherein said recess in each of said first and second end faces, and the corresponding first and second impact members are sized and configured so that the corresponding first and second impact surface is disposed entirely within the recess in the corresponding first and second end face.

22. The pneumatic impactor of claim 14, wherein:
the piston includes a first axial end and a second axial end, each axial end including an outwardly facing contact surface and an outwardly facing piston surface,
wherein the outwardly facing contact surface at the first axial end is arranged to strike the first impact member and the piston surface at the first axial end is arranged to contact the first end face, and
the outwardly facing contact surface at the second axial end is arranged to strike the second impact member and the piston surface at the second axial end is arranged to contact the second end face.

23. The pneumatic impactor of claim 22, wherein:
the piston surface of each end of the piston is a ring-shaped surface; and
the outwardly facing contact surface of each end of the piston is a ring-shaped surface having a smaller diameter than the ring-shaped surface of the piston surface.

24. The pneumatic impactor of claim 23, wherein:
the piston surface and outwardly facing contact surface of each of the first axial end and second axial end of said piston are coplanar; and
said recess in each of said first and second end faces, and the corresponding first and second impact members are sized and configured so that the corresponding first and second impact surface is disposed entirely within the recess in the corresponding first and second end face.

25. The pneumatic impactor of claim 23, wherein:
the piston surface and contact surface of each end are not coplanar, with the contact surface axially recessed relative to the piston surface; and
said recess in each of said first and second end faces, and the corresponding first and second impact members are sized and configured so that the corresponding first and second impact surface is partially disposed within the recess in the corresponding first and second end face with a portion outside the recess.

* * * * *